US010327953B2

United States Patent
Srinivasan et al.

(10) Patent No.: US 10,327,953 B2
(45) Date of Patent: Jun. 25, 2019

(54) LASER EYE SURGERY LENS FRAGMENTATION

(71) Applicant: OptiMedica Corporation, Sunnyvale, CA (US)

(72) Inventors: Rajeshwari Srinivasan, San Carlos, CA (US); Javier G. Gonzalez, Palo Alto, CA (US); Erik C. Kramme, Glenview, IL (US)

(73) Assignee: OPTIMEDICA CORPORATION, Santa Ana, CA (US)

( * ) Notice: Subject to any disclaimer, the term of this patent is extended or adjusted under 35 U.S.C. 154(b) by 224 days.

(21) Appl. No.: 14/885,596

(22) Filed: Oct. 16, 2015

(65) Prior Publication Data

US 2016/0106588 A1 Apr. 21, 2016

Related U.S. Application Data

(60) Provisional application No. 62/065,469, filed on Oct. 17, 2014.

(51) Int. Cl.
 *A61F 9/008* (2006.01)
 *A61B 3/10* (2006.01)

(52) U.S. Cl.
 CPC ............ *A61F 9/0084* (2013.01); *A61B 3/102* (2013.01); *A61F 9/00804* (2013.01);
 (Continued)

(58) Field of Classification Search
 CPC .. A61F 9/008; A61F 9/00812; A61F 9/00825; A61F 9/00834;
 (Continued)

(56) References Cited

U.S. PATENT DOCUMENTS

| 5,720,894 A | 2/1998 | Neev et al. |
| 5,957,915 A | 9/1999 | Trost |

(Continued)

FOREIGN PATENT DOCUMENTS

| WO | 2009059251 A2 | 5/2009 |
| WO | 2011035063 A1 | 3/2011 |
| WO | 2012040196 A1 | 3/2012 |

OTHER PUBLICATIONS

International Search Report and Written Opinion for Application No. PCT/US2015/056029, dated Jan. 28, 2016, 15 pages.

*Primary Examiner* — Ahmed M Farah
(74) *Attorney, Agent, or Firm* — Johnson & Johnson Surgical Vision, Inc.

(57) ABSTRACT

A laser eye surgery system includes a laser to generate a laser beam. A spatial measurement system generates a measurement beam and measure a spatial disposition of an eye. A processor is coupled to the laser and the spatial measurement system, the processor comprising a tangible medium embodying instructions to determine a spatial model of the eye in an eye coordinate reference system based on the measurement beam. The spatial model is mapped from the eye coordinate reference system to a machine coordinate reference system. A laser fragmentation pattern is determined based on a plurality of laser fragmentation parameters. The laser fragmentation pattern and the spatial model is rotated by a first rotation angle such that the spatial model is aligned with the reference axis of the machine coordinate reference system and the rotated laser fragmentation pattern is aligned with the corneal incision.

8 Claims, 27 Drawing Sheets

(52) U.S. Cl.
CPC ...... *A61F 9/00825* (2013.01); *A61F 9/00827* (2013.01); *A61F 2009/0087* (2013.01); *A61F 2009/00851* (2013.01); *A61F 2009/00853* (2013.01); *A61F 2009/00855* (2013.01); *A61F 2009/00872* (2013.01); *A61F 2009/00882* (2013.01); *A61F 2009/00887* (2013.01)

(58) Field of Classification Search
CPC .... A61F 2009/00861; A61F 2009/0087; A61F 2009/00885; A61F 2009/0887; A61F 2009/00889
USPC ............ 606/4, 6, 10–12, 167; 623/4.1, 6.11, 623/6.18–6.22; 604/19–22; 128/989
See application file for complete search history.

(56) References Cited

U.S. PATENT DOCUMENTS

| | | |
|---|---|---|
| 5,984,916 A | 11/1999 | Lai |
| 6,019,472 A | 2/2000 | Koester et al. |
| 6,454,761 B1 | 9/2002 | Freedman |
| 7,655,002 B2 | 2/2010 | Myers et al. |
| 7,717,907 B2 | 5/2010 | Ruiz et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 9,775,743 B2 * | 10/2017 | Clauson ............... A61F 9/00825 |
| 2011/0319873 A1 | 12/2011 | Raksi et al. |
| 2011/0319875 A1 | 12/2011 | Loesel et al. |
| 2012/0271286 A1 * | 10/2012 | Curatu ................ A61F 9/00825 606/5 |
| 2012/0330290 A1 * | 12/2012 | Gray ....................... A61F 9/008 606/4 |
| 2014/0114297 A1 * | 4/2014 | Woodley ................. A61F 9/008 606/6 |
| 2017/0189233 A1 * | 7/2017 | Dewey ................ A61F 9/00827 |

* cited by examiner

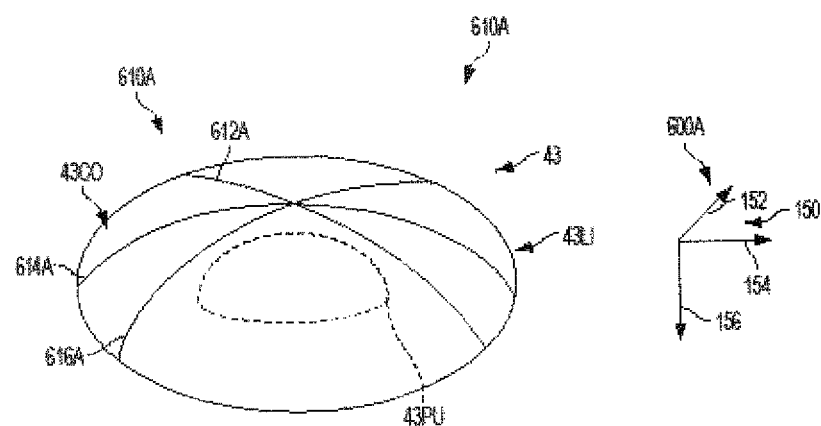
FIG. 6A1
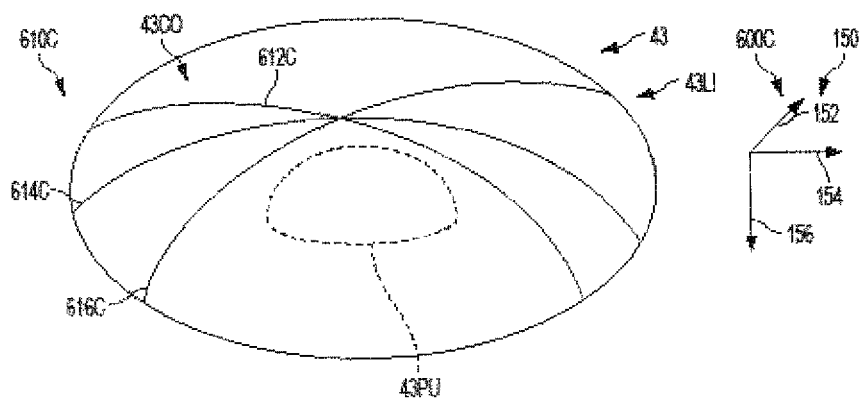
FIG. 6C1

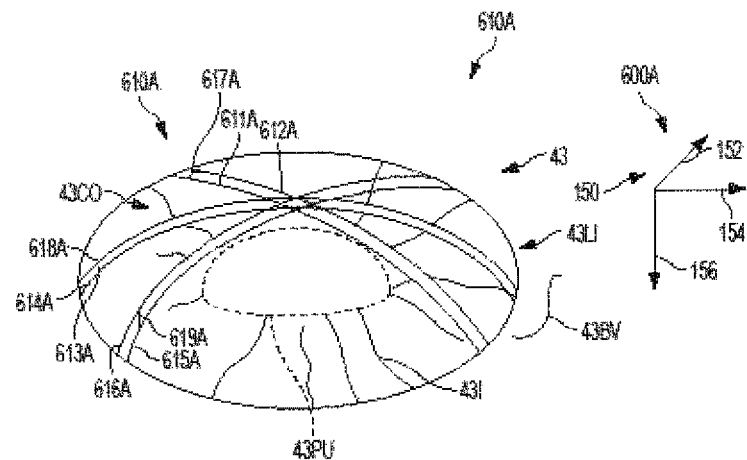
FIG. 6A2
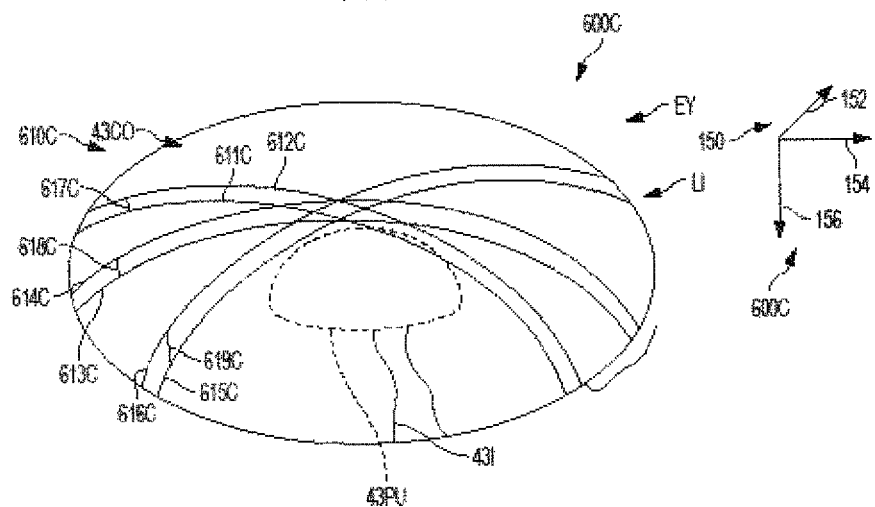
FIG. 6C2

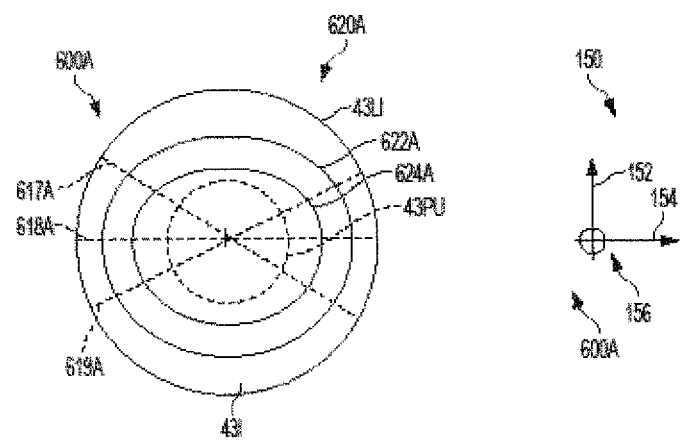
FIG. 6A3
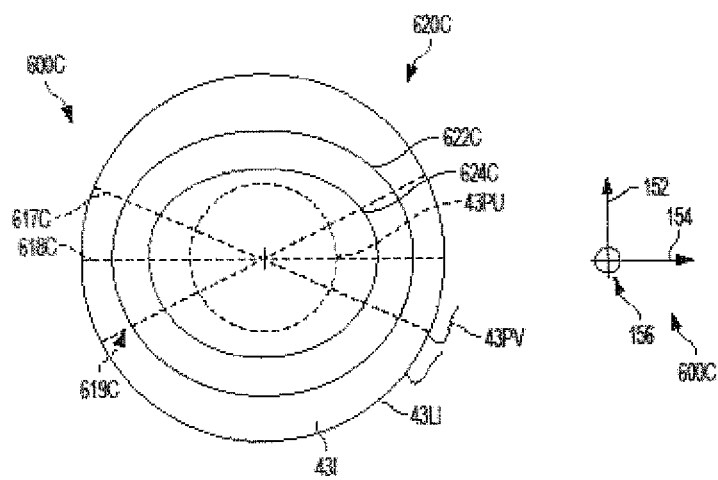
FIG. 6C3

LASER EYE SURGERY LENS FRAGMENTATION

CROSS REFERENCE TO RELATED APPLICATIONS

This application is a non-provisional application and claims the benefit under 35 U.S.C. § 119(e) of U.S. Provisional Application Ser. No. 62/065,469, filed Oct. 17, 2014, which is incorporated herein in its entirety as if fully set forth.

The subject matter of the present disclosure is related to the following patent applications: U.S. application Ser. No. 14/069,042 filed on Oct. 31, 2013; U.S. application Ser. No. 14/509,850 filed on Oct. 8, 2014; U.S. application Ser. No. 14/256,307 filed on Apr. 18, 2014; U.S. application Ser. No. 14/255,430 filed on Apr. 17, 2014, the entire disclosures of which are incorporated herein by reference and suitable for combination in accordance with embodiments disclosed herein.

BACKGROUND

The present disclosure relates generally to photodisruption induced by a pulsed laser beam and the location of the photodisruption so as to treat a material, such as a tissue of an eye. Although specific reference is made to cutting tissue for surgery such as eye surgery, embodiments as described herein can be used in many ways with many materials to treat one or more of many materials, such as cutting of optically transparent materials.

Cutting of materials can be done mechanically with chisels, knives, scalpels and other tools such as surgical tools. However, prior methods and apparatus of cutting can be less than desirable and provide less than ideal results in at least some instances. For example, at least some prior methods and apparatus for cutting materials such as tissues may provide a somewhat rougher surface than would be ideal. Pulsed lasers can be used to cut one or more of many materials and have been used for laser surgery to cut tissue.

The prior methods and apparatus to incise tissue with laser beams can be less than ideal in at least some instances. For example, the laser beam may incise tissue at a targeted location that is sub-optimal for a surgeon to further operate on.

An example of an eye surgery in which embodiments may be applied is described below. Cataract extraction is one of the most commonly performed surgical procedures in the world. A cataract is formed by opacification of the crystalline lens or its envelope—the lens capsule—of the eye. The cataract obstructs passage of light through the lens. A cataract can vary in degree from slight to complete opacity. Early in the development of an age-related cataract the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. Cataracts are potentially blinding if untreated.

A common cataract treatment involves replacing the opaque crystalline lens with an artificial intraocular lens (IOL). Presently, an estimated 15 million cataract surgeries per year are performed worldwide. The cataract treatment market is composed of various segments including intraocular lenses for implantation, viscoelastic polymers to facilitate surgical procedures, and disposable instrumentation including ultrasonic phacoemulsification tips, tubing, various knives, and forceps.

Presently, cataract surgery is typically performed using a technique termed phacoemulsification in which an ultrasonic tip and associated irrigation and aspiration ports is used to sculpt the relatively hard nucleus of the lens to facilitate removal through an opening made in the anterior lens capsule. The nucleus of the lens is contained within an outer membrane of the lens that is referred to as the lens capsule. Access to the lens nucleus can be provided by performing an anterior capsulotomy in which a small (often round) hole is formed in the anterior side of the lens capsule. Access to the lens nucleus can also be provided by performing a manual continuous curvilinear capsulorhexis (CCC) procedure.

The lens may then be fragmented by segmenting and/or softening the lens by a laser to aid in removal by a phacoemulsification tip. Removal of the lens with the phacoemulsification tip is then performed through a primary corneal incision, for instance. After removal of the lens nucleus, a synthetic foldable intraocular lens (IOL) can be inserted into the remaining lens capsule of the eye. Typically, the IOL is held in place by the edges of the anterior capsule and the capsular bag. The IOL may also be held by the posterior capsule, either alone or in unison with the anterior capsule.

One of the most challenging and critical steps in the cataract extraction procedure is the extraction of the nucleus of the lens. After a primary incision is provided for insertion of the phaco tip, the surgeon generally first skewers a portion of the lens with the phaco tip. The portion of the lens attached to the phaco tip may then be pulled up and vacuum suctioned for removal. The remaining portion of the lens is rotated to align with the incision for the phaco tip to purchase. This process is repeated until the lens is fully extracted, and suffers from complications related to rotation, softening, and size of the lens.

First, the rotation of the lens by the surgeon may undesirably break up the lens, thereby complicating the lens removal process. Surgeons typically manipulate the phacoemulsification tip to rotate the lens nucleus to aid in efficient removal the lens nucleus. If the lens is fragmented in preparation for extraction, the surgeon typically first rotates the lens fragmentation pattern to align with the primary incision. This rotation may result in portions of the lens crumbling off as well as other damage. If this occurs, the surgeon must make additional attempts to find and acquire these smaller lens pieces, thus increasing the possibility of complications such as engagement with the posterior capsule.

Second, the large size of the removed lens pieces is cumbersome and places additional burden on surgeons. The standard capsulotomy is 5 millimeter in diameter, thereby providing an opening of about 2.5 millimeter for the phaco tip and portion of lens to be removed. However, the lens diameter is typically 8-10 millimeters such that even if the lens is segmented into four quadrants, the dimensions of the lens does not allow for easy removal through the phaco incision. Accordingly, the removal of the initial lens piece poses a particular challenge. Removal is even more difficult if the lens is not segmented, sculpted, debulked, and/or fully separated.

Third, lenses softened by a laser beam are harder to remove since softened lens pieces are more likely to fall apart, especially during extraction of the initial lens piece. Softened pieces are also more likely to crumble when rotated. The lens becomes thinned as pieces of a softened lens are broken off, with subsequent attempts at purchasing the lens being required.

In light of the above, it would be desirable to have an improved apparatus and method of treating materials with laser beams, such as the surgical cutting of tissue to treat cataracts and refractive errors of the eye. At least some of the above deficiencies of the prior methods and apparatus are overcome by the embodiments described herein.

SUMMARY

Embodiments as described herein provide improved treatment of materials such as tissue. Improved eye surgery systems, and related methods, are provided. In one aspect, a laser eye surgery system includes a laser to generate a laser beam. A spatial measurement system is provided to generate a measurement beam and measure a spatial disposition of an eye. A processor is coupled to the laser and the spatial measurement system, the processor comprising a tangible medium embodying instructions to determine a spatial model of the eye in an eye coordinate reference system based on the measurement beam. The processor maps the spatial model from the eye coordinate reference system to a machine coordinate reference system. The processor receives a rotation angle of a corneal incision relative to a reference axis of the machine coordinate reference system. The processor determines a laser fragmentation pattern based on a plurality of laser fragmentation parameters. The processor determines a first rotation angle based on the rotation angle of the corneal incision and a rotation angle of the laser fragmentation pattern relative to the reference axis of the machine coordinate reference system. The processor rotates the spatial model by a negative of the first rotation angle. The processor rotates the laser fragmentation pattern and the spatial model by the determined first rotation angle such that the spatial model is aligned with the reference axis of the machine coordinate reference system and the rotated laser fragmentation pattern is aligned with the corneal incision.

Variations of the laser eye surgery system are provided. For example, the laser fragmentation pattern defines a first lens portion to be first extracted that is aligned opposite the corneal incision. The laser fragmentation pattern is asymmetrical. The lens fragmentation pattern includes a first portion and a second portion having at least one of a different segmentation pattern and softening pattern. The lens fragmentation pattern includes a first unsoftened portion and a second softened portion. The lens fragmentation pattern includes a first portion defining two octants and a second portion defining three quadrants. The lens fragmentation pattern includes a first portion defining two unsoftened octants and a second portion defining three softened quadrants. The laser beam is generated based on the rotated laser fragmentation pattern. The first rotation angle is based on user input.

In some embodiments, a method of generating a lens fragmentation pattern includes determining a spatial model of the eye in an eye coordinate reference system based on the measurement beam. The spatial model is mapped from the eye coordinate reference system to a machine coordinate reference system. A rotation angle of a corneal incision relative to a reference axis of the machine coordinate reference system is received. A laser fragmentation pattern is determined based on a plurality of laser fragmentation parameters. A first rotation angle is determined based on the rotation angle of the corneal incision and a rotation angle of the laser fragmentation pattern relative to the reference axis of the machine coordinate reference system. The spatial model is rotated by a negative of the first rotation angle. The laser fragmentation pattern and the spatial model are rotated by the determined first rotation angle such that the spatial model is aligned with the reference axis of the machine coordinate reference system and the rotated laser fragmentation pattern is aligned with the corneal incision. A laser beam is generated based on the laser fragmentation pattern.

Variations of the method are provided. The laser fragmentation pattern defines a first lens portion to be extracted first that is aligned opposite the corneal incision. The laser fragmentation pattern is asymmetrical. The lens fragmentation pattern includes a first portion and a second portion having at least one of a different segmentation pattern and softening pattern. The lens fragmentation pattern includes a first unsoftened portion and a second softened portion. The lens fragmentation pattern includes a first portion defining two octants and a second portion defining three quadrants. The lens fragmentation pattern includes a first portion defining two unsoftened octants and a second portion defining three softened quadrants. The first rotation angle is based on user input.

In some embodiments, a method of treating an object with a laser beam includes measuring a plurality of characteristics of the object by an object sensor. A model of the object is determined based on the measured characteristics. A rotation angle of an incision relative to a reference coordinate space is received. A laser fragmentation pattern for treating the object is generated. The laser fragmentation pattern is rotated by the received rotation angle relative to the reference coordinate space. A laser beam is applied based on the rotated laser fragmentation pattern to the object. The model is rotated by a negative of the received rotation angle, wherein the model is aligned with the reference coordinate space and the laser fragmentation pattern is aligned with the incision.

In some embodiments, a method of generating a lens fragmentation pattern includes measuring a plurality of characteristics of an eye by a laser surgery system. A spherical model of the eye is determined. Lens segmentation boundaries are determined based on the spherical model. A rotation angle of a corneal incision is received relative to a reference coordinate space. A laser fragmentation pattern for the eye is generated. The laser fragmentation pattern is rotated relative to the received rotation angle. A laser beam is applied based on the rotated laser fragmentation pattern on the eye.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A1 shows corneal profile data for the coordinate system and image of FIG. 6A;

FIG. 6A2 shows corneal thickness profile data for the coordinate system and images of FIGS. 6A and 6A1;

FIG. 6A3 shows corneal thickness profile maps for the coordinate system and images of FIGS. 6A, 6A1 and 6A2;

FIG. 6C1 shows corneal profile data for the coordinate system and image of FIG. 6C;

FIG. 6C2 shows corneal thickness profile data for the coordinate system and images of FIGS. 6C and 6C1.

FIG. 6C3 shows corneal thickness profile maps for the coordinate system and images of FIGS. 6C, 6C1 and 6C2;

DETAILED DESCRIPTION

Figure 1:
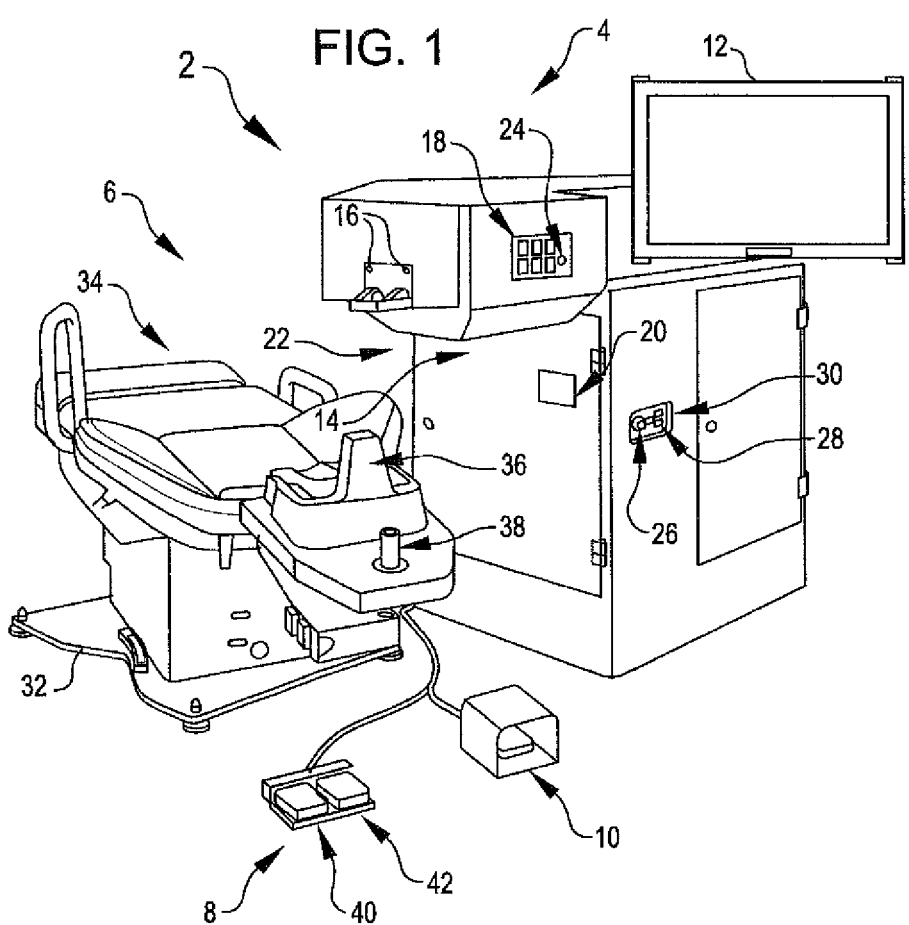
FIG. 1 is a perspective view showing a laser eye surgery system, in accordance with many embodiments.

Methods and systems related to laser eye surgery are disclosed, and laser cataract surgery in particular. In many embodiments, a laser is used to form precise incisions in the cornea, in the lens capsule, and/or in the crystalline lens nucleus. Although specific reference is made to tissue treatment for laser eye surgery, such as cataract surgery, embodiments as described herein can be combined in one or more of many ways with many surgical procedures and devices, such as orthopedic surgery, robotic surgery, and microkeratomes.

The embodiments as describe herein are particularly well suited for treating tissue, such as with the surgical treatment of tissue. In many embodiments, the tissue comprises an optically transmissive tissue, such as tissue of an eye. The embodiments as described herein can be combined in many ways with one or more of many known surgical procedures such as cataract surgery, laser assisted in situ keratomileusis (hereinafter "LASIK"), laser assisted subepithelial keratectomy (hereinafter "LASEK"). The embodiments as described herein are also particularly well suited for retinal surgery, for example.

The embodiments as described herein are particularly well suited for calibrating laser surgery systems capable of providing a treatment within a three dimensional volume, and the target locations and marks can be defined such that as least a portion of the treatment is within the three dimensional volume defined with the plurality of target locations.

In many embodiments, the laser eye surgery system comprises a processor having a tangible medium embodying instructions to track the location of the eye in response to marks of the eye provided with pulses of the laser beam.

Methods and systems related to laser eye surgery are disclosed. A laser is used to form precise incisions in the cornea, in the lens capsule, and/or in the crystalline lens nucleus. In many embodiments, a laser eye surgery system includes a laser cutting subsystem to produce a laser pulse treatment beam to incise tissue within the eye, a ranging subsystem to measure the spatial disposition of external and internal structures of the eye in which incisions can be formed, an alignment subsystem, and shared optics operable to scan the treatment beam, a ranging subsystem beam, and/or an alignment beam relative to the laser eye surgery system. The alignment subsystem can include a video subsystem that can be used to, for example, provide images of the eye during docking of the eye to the laser eye surgery system and also provide images of the eye once the docking process is complete. In many embodiments, a liquid interface is used between a patient interface lens and the eye.

As used herein, the terms anterior and posterior refers to known orientations with respect to the patient. Depending on the orientation of the patient for surgery, the terms anterior and posterior may be similar to the terms upper and lower, respectively, such as when the patient is placed in a supine position on a bed. The terms distal and anterior may refer to an orientation of a structure from the perspective of the user, such that the terms proximal and distal may be similar to the terms anterior and posterior when referring to a structure placed on the eye, for example. A person of ordinary skill in the art will recognize many variations of the orientation of the methods and apparatus as described herein, and the terms anterior, posterior, proximal, distal, upper, and lower are used merely by way of example.

As used herein, the terms first and second are used to describe structures and methods without limitation as to the order of the structures and methods which can be in any order, as will be apparent to a person of ordinary skill in the art based on the teachings provided herein.

As used herein light encompasses electromagnetic radiation having one or more wavelengths in one or more of the ultraviolet, visible or infrared portions of the electromagnetic spectrum.

As used herein in situ encompasses in position and refers to measurements and treatments made with an object located in substantially the same position.

As used herein, the terms fragmentation and segmentation are used interchangeably throughout this disclosure and refer to photodisruption applied to treat a material. Fragmentation may include softening.

FIG. 1 shows a laser eye surgery system 2, in accordance with many embodiments, operable to form precise incisions in the cornea, in the lens capsule, and/or in the crystalline lens nucleus. The system 2 includes a main unit 4, a patient chair 6, a dual function footswitch 8, and a laser footswitch 10.

The main unit 4 includes many primary subsystems of the system 2. For example, externally visible subsystems include a touch-screen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30.

The patient chair 6 includes a base 32, a patient support bed 34, a headrest 36, a positioning mechanism, and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The patient chair 6 allows for tilt articulation of the patient's legs, torso, and head using manual adjustments. The patient chair 6 accommodates a patient load position, a suction ring capture position, and a patient treat position. In the patient load position, the chair 6 is rotated out from under the main unit 4 with the patient chair back in an upright position and patient footrest in a lowered position. In the suction ring capture position, the chair is rotated out from under the main unit 4 with the patient chair back in reclined position and patient footrest in raised position. In the patient treat position, the chair is rotated under the main unit 4 with the patient chair back in reclined position and patient footrest in raised position.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

In many embodiments, the patient control joystick 38 is a proportional controller. For example, moving the joystick a small amount can be used to cause the chair to move slowly. Moving the joystick a large amount can be used to cause the chair to move faster. Holding the joystick at its maximum travel limit can be used to cause the chair to move at the maximum chair speed. The available chair speed can be reduced as the patient approaches the patient interface assembly 14.

The emergency stop button 26 can be pushed to stop emission of all laser output, release vacuum that couples the patient to the system 2, and disable the patient chair 6. The stop button 26 is located on the system front panel, next to the key switch 28.

The key switch 28 can be used to enable the system 2. When in a standby position, the key can be removed and the system is disabled. When in a ready position, the key enables power to the system 2.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

In many embodiments, the system 2 includes external communication connections. For example, the system 2 can include a network connection (e.g., an RJ45 network connection) for connecting the system 2 to a network. The network connection can be used to enable network printing of treatment reports, remote access to view system performance logs, and remote access to perform system diagnostics. The system 2 can include a video output port (e.g., HDMI) that can be used to output video of treatments performed by the system 2. The output video can be displayed on an external monitor for, for example, viewing by family members and/or training. The output video can also be recorded for, for example, archival purposes. The system 2 can include one or more data output ports (e.g., USB) to, for example, enable export of treatment reports to a data storage device. The treatments reports stored on the data storage device can then be accessed at a later time for any suitable purpose such as, for example, printing from an external computer in the case where the user without access to network based printing.

Figure 2:
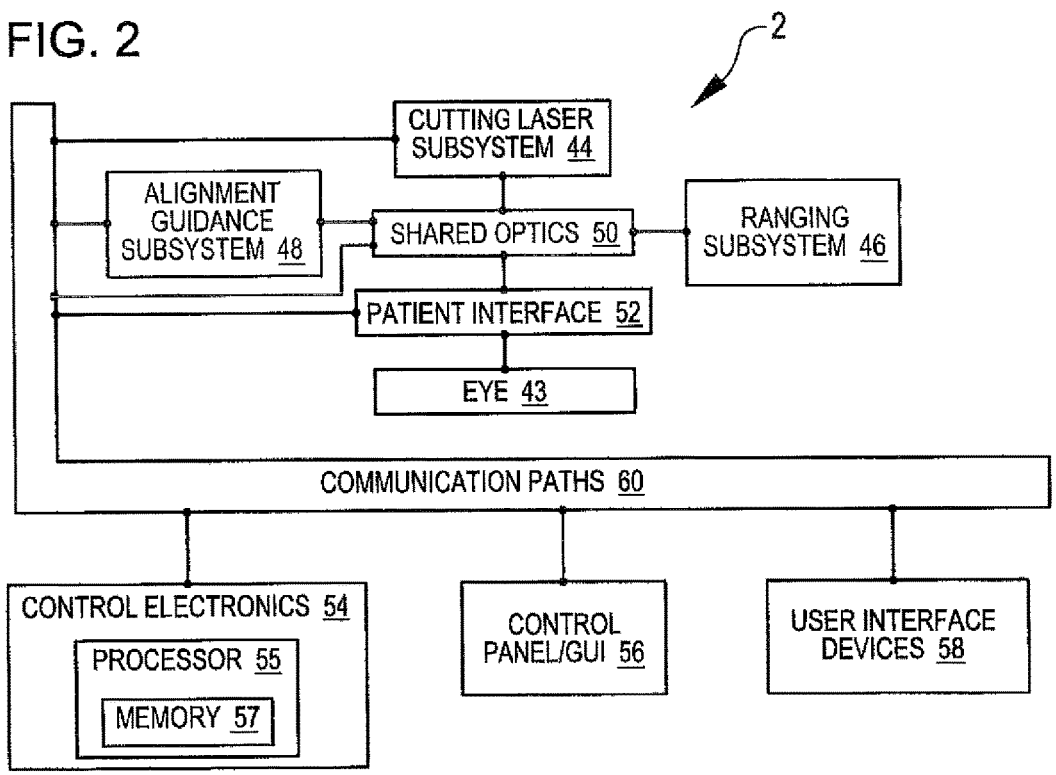
FIG. 2 is a simplified block diagram showing a top level view of the configuration of a laser eye surgery system, in accordance with many embodiments.

FIG. 2 shows a simplified block diagram of the system 2 coupled with a patient eye 43. The patient eye 43 comprises a cornea, a lens, and an iris. The iris defines a pupil of the eye 43 that may be used for alignment of eye 43 with system 2. The system 2 includes a cutting laser subsystem 44, a ranging subsystem 46, an alignment guidance system 48, shared optics 50, a patient interface 52, control electronics 54, a control panel/GUI 56, user interface devices 58, and communication paths 60. The control electronics 54 is operatively coupled via the communication paths 60 with the cutting laser subsystem 44, the ranging subsystem 46, the alignment guidance subsystem 48, the shared optics 50, the patient interface 52, the control panel/GUI 56, and the user interface devices 58.

In many embodiments, the cutting laser subsystem 44 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required as compared to the level required for ultrasound fragmentation of the lens nucleus and as compared to laser pulses having longer durations.

The cutting laser subsystem 44 can produce laser pulses having a wavelength suitable to the configuration of the system 2. As a non-limiting example, the system 2 can be configured to use a cutting laser subsystem 44 that produces laser pulses having a wavelength from 1020 nm to 1050 nm. For example, the cutting laser subsystem 44 can have a diode-pumped solid-state configuration with a 1030 (+/−5) nm center wavelength.

The cutting laser subsystem 44 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly to adapt the beam containing the laser pulses to the characteristics of the system 2 and a fixed optical relay to transfer the laser pulses over a distance while accommodating laser pulse beam positional and/or directional variability, thereby providing increased tolerance for component variation.

The ranging subsystem 46 is configured to measure the spatial disposition of eye structures in three dimensions. The measured eye structures can include the anterior and posterior surfaces of the cornea, the anterior and posterior portions of the lens capsule, the iris, and the limbus. In many embodiments, the ranging subsystem 46 utilizes optical coherence tomography (OCT) imaging. As a non-limiting example, the system 2 can be configured to use an OCT imaging system employing wavelengths from 780 nm to 970 nm. For example, the ranging subsystem 46 can include an OCT imaging system that employs a broad spectrum of wavelengths from 810 nm to 850 nm. Such an OCT imaging system can employ a reference path length that is adjustable to adjust the effective depth in the eye of the OCT measurement, thereby allowing the measurement of system components including features of the patient interface that lie anterior to the cornea of the eye and structures of the eye that range in depth from the anterior surface of the cornea to the posterior portion of the lens capsule and beyond.

The alignment guidance subsystem 48 can include a laser diode or gas laser that produces a laser beam used to align optical components of the system 2. The alignment guidance subsystem 48 can include LEDs or lasers that produce a fixation light to assist in aligning and stabilizing the patient's eye during docking and treatment. The alignment guidance subsystem 48 can include a laser or LED light source and a detector to monitor the alignment and stability of the actuators used to position the beam in X, Y, and Z. The alignment guidance subsystem 48 can include a video system that can be used to provide imaging of the patient's eye to facilitate docking of the patient's eye 43 to the patient interface 52. The imaging system provided by the video system can also be used to direct via the GUI the location of cuts. The imaging provided by the video system can additionally be used during the laser eye surgery procedure to monitor the progress of the procedure, to track movements of the patient's eye 43 during the procedure, and to measure the location and size of structures of the eye such as the pupil and/or limbus.

The shared optics 50 provides a common propagation path that is disposed between the patient interface 52 and each of the cutting laser subsystem 44, the ranging subsystem 46, and the alignment guidance subsystem 48. In many embodiments, the shared optics 50 includes beam combiners to receive the emission from the respective subsystem (e.g., the cutting laser subsystem 44, and the alignment guidance subsystem 48) and redirect the emission along the common propagation path to the patient interface. In many embodiments, the shared optics 50 includes an objective lens assembly that focuses each laser pulse into a focal point. In many embodiments, the shared optics 50 includes scanning mechanisms operable to scan the respective emission in three dimensions. For example, the shared optics can include an XY-scan mechanism(s) and a Z-scan mechanism. The XY-scan mechanism(s) can be used to scan the respective emission in two dimensions transverse to the propagation direction of the respective emission. The Z-scan mechanism can be used to vary the depth of the focal point within the eye 43. In many embodiments, the scanning mechanisms are disposed between the laser diode and the objective lens such that the scanning mechanisms are used to scan the alignment laser beam produced by the laser diode. In contrast, in many embodiments, the video system is disposed between the scanning mechanisms and the objective lens such that the scanning mechanisms do not affect the image obtained by the video system.

The patient interface 52 is used to restrain the position of the patient's eye 43 relative to the system 2. In many embodiments, the patient interface 52 employs a suction ring that is vacuum attached to the patient's eye 43. The suction ring is then coupled with the patient interface 52, for example, using vacuum to secure the suction ring to the patient interface 52. In many embodiments, the patient interface 52 includes an optically transmissive structure having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface and the patient's cornea and forms part of a transmission path between the shared optics 50 and the patient's eye 43. The optically transmissive structure may comprise a lens 96 having one or more curved surfaces. Alternatively, the patient interface 22 may comprise an optically transmissive structure having one or more substantially flat surfaces such as a parallel plate or wedge. In many embodiments, the patient interface lens is disposable and can be replaced at any suitable interval, such as before each eye treatment.

The control electronics 54 controls the operation of and can receive input from the cutting laser subsystem 44, the ranging subsystem 46, the alignment guidance subsystem 48, the patient interface 52, the control panel/GUI 56, and the user interface devices 58 via the communication paths 60. The communication paths 60 can be implemented in any suitable configuration, including any suitable shared or dedicated communication paths between the control electronics 54 and the respective system components.

The control electronics 54 can include any suitable components, such as one or more processor, one or more field-programmable gate array (FPGA), and one or more memory storage devices. In many embodiments, the control electronics 54 controls the control panel/GUI 56 to provide for pre-procedure planning according to user specified treatment parameters as well as to provide user control over the laser eye surgery procedure.

The control electronics 54 may comprise a processor/controller 55 (referred to herein as a processor) that is used to perform calculations related to system operation and provide control signals to the various system elements. A computer readable medium 57 (also referred to as a database or a memory) is coupled to the processor 55 in order to store data used by the processor and other system elements. The processor 55 interacts with the other components of the system as described more fully throughout the present specification. In an embodiment, the memory 57 can include a look up table that can be utilized to control one or more components of the laser system as described herein.

The processor 55 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 57 can be local or distributed as appropriate to the particular application. Memory 57 may include a number of memories including a main random access memory (RAM) for storage of instructions and data during program execution and a read only memory (ROM) in which fixed instructions are stored. Thus, memory 57 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 58 can include any suitable user input device suitable to provide user input to the control electronics 54. For example, the user interface devices 58 can include devices such as, for example, the dual function footswitch 8, the laser footswitch 10, the docking control keypad 18, the patient interface radio frequency identification (RFID) reader 20, the emergency laser stop button 26, the key switch 28, and the patient chair joystick control 38.

Figure 3:
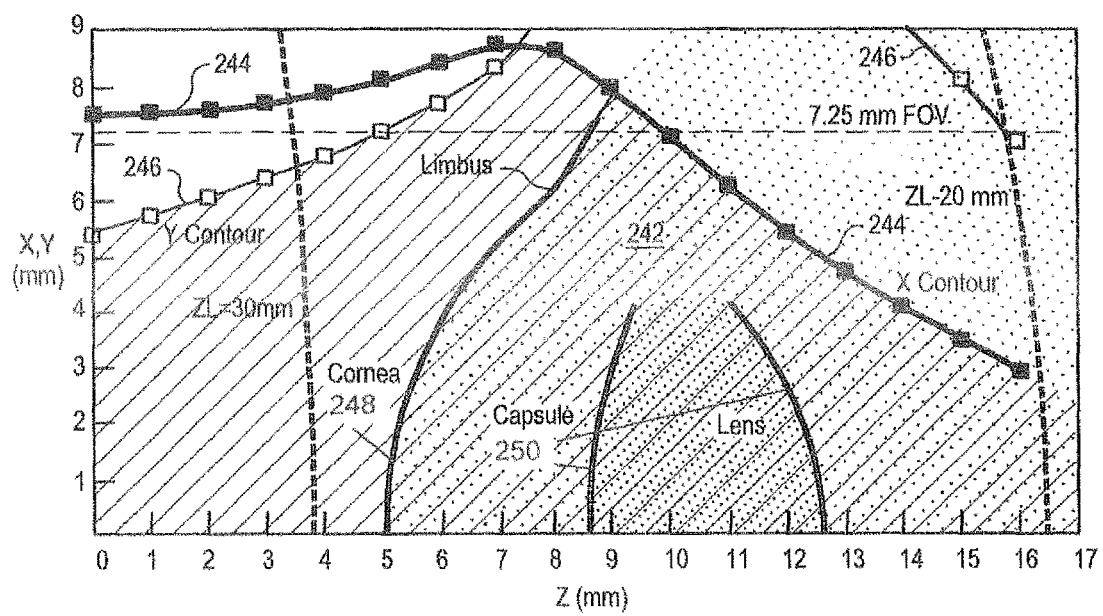
FIG. 3 diagrammatically illustrates a volume within an eye in which incisions can be formed by a laser eye surgery system, in accordance with many embodiments.

FIG. 3 is a simplified block diagram illustrating an assembly 62, in accordance with many embodiments, that can be included in the system 2. The assembly 62 is a non-limiting example of suitable configurations and integration of the cutting laser subsystem 44, the ranging subsystem 46, the alignment guidance subsystem 48, the shared optics 50, and the patient interface 52. Other configurations and integration of the cutting laser subsystem 44, the ranging subsystem 46, the alignment guidance subsystem 48, the shared optics 50, and the patient interface 52 may be possible and may be apparent to a person of skill in the art.

The assembly 62 is operable to project and scan optical beams into the patient's eye 43. The cutting laser subsystem 44 includes an ultrafast (UF) laser 64 (e.g., a femtosecond laser). Using the assembly 62, optical beams can be scanned in the patient's eye 43 in three dimensions: X, Y, Z. For example, short-pulsed laser light generated by the UF laser 64 can be focused into eye tissue to produce dielectric breakdown to cause photodisruption around the focal point (the focal zone), thereby rupturing the tissue in the vicinity of the photo-induced plasma. In the assembly 62, the wavelength of the laser light can vary between 800 nm to 1200 nm and the pulse width of the laser light can vary from 10 fs to 10000 fs. The pulse repetition frequency can also vary from 10 kHz to 500 kHz. Safety limits with regard to unintended damage to non-targeted tissue bound the upper limit with regard to repetition rate and pulse energy. Threshold energy, time to complete the procedure, and stability can bound the lower limit for pulse energy and repetition rate. The peak power of the focused spot in the eye 43 and specifically within the crystalline lens and the lens capsule of the eye is sufficient to produce optical breakdown and initiate a plasma-mediated ablation process. Near-infrared wavelengths for the laser light are preferred because linear optical absorption and scattering in biological tissue is reduced for near-infrared wavelengths. As an example, the laser 64 can be a repetitively pulsed 1031 nm device that produces pulses with less than 600 fs duration at a repetition rate of 120 kHz (+/−5%) and individual pulse energy in the 1 to 20 micro joule range.

The cutting laser subsystem 44 is controlled by the control electronics 54 and the user, via the control panel/GUI 56 and the user interface devices 58, to create a laser pulse beam 66. The control panel/GUI 56 is used to set system operating parameters, process user input, display gathered information such as images of ocular structures, and display representations of incisions to be formed in the patient's eye 43.

The generated laser pulse beam 66 proceeds through a zoom assembly 68. The laser pulse beam 66 may vary from unit to unit, particularly when the UF laser 64 may be obtained from different laser manufacturers. For example, the beam diameter of the laser pulse beam 66 may vary from unit to unit (e.g., by +/−20%). The beam may also vary with regard to beam quality, beam divergence, beam spatial circularity, and astigmatism. In many embodiments, the zoom assembly 68 is adjustable such that the laser pulse beam 66 exiting the zoom assembly 68 has consistent beam diameter and divergence unit to unit.

After exiting the zoom assembly 68, the laser pulse beam 66 proceeds through an attenuator 70. The attenuator 70 is used to adjust the transmission of the laser beam and thereby the energy level of the laser pulses in the laser pulse beam 66. The attenuator 70 is controlled via the control electronics 54.

After exiting the attenuator 70, the laser pulse beam 66 proceeds through an aperture 72. The aperture 72 sets the outer useful diameter of the laser pulse beam 66. In turn the zoom determines the size of the beam at the aperture location and therefore the amount of light that is transmitted. The amount of transmitted light is bounded both high and low. The upper is bounded by the requirement to achieve the highest numerical aperture achievable in the eye. High NA promotes low threshold energies and greater safety margin for untargeted tissue. The lower is bound by the requirement for high optical throughput. Too much transmission loss in the system shortens the lifetime of the system as the laser output and system degrades over time. Additionally, consistency in the transmission through this aperture promotes stability in determining optimum settings (and sharing of) for each procedure. Typically to achieve optimal performance the transmission through this aperture as set to be between 88% to 92%.

After exiting the aperture 72, the laser pulse beam 66 proceeds through two output pickoffs 74. Each output pickoff 74 can include a partially reflecting mirror to divert a portion of each laser pulse to a respective output monitor 76. Two output pickoffs 74 (e.g., a primary and a secondary) and respective primary and secondary output monitors 76 are used to provide redundancy in case of malfunction of the primary output monitor 76.

After exiting the output pickoffs 74, the laser pulse beam 66 proceeds through a system-controlled shutter 78. The system-controlled shutter 78 ensures on/off control of the laser pulse beam 66 for procedural and safety reasons. The two output pickoffs precede the shutter allowing for monitoring of the beam power, energy, and repetition rate as a pre-requisite for opening the shutter.

After exiting the system-controlled shutter 78, the optical beam proceeds through an optics relay telescope 80. The optics relay telescope 80 propagates the laser pulse beam 66 over a distance while accommodating positional and/or directional variability of the laser pulse beam 66, thereby providing increased tolerance for component variation. As an example, the optical relay can be a keplerian afocal telescope that relays an image of the aperture position to a conjugate position near to the XY galvo mirror positions. In this way, the position of the beam at the XY galvo location is invariant to changes in the beams angle at the aperture position. Similarly the shutter does not have to precede the relay and may follow after or be included within the relay.

After exiting the optics relay telescope 80, the laser pulse beam 66 is transmitted to the shared optics 50, which propagates the laser pulse beam 66 to the patient interface 52. The laser pulse beam 66 is incident upon a beam combiner 82, which reflects the laser pulse beam 66 while transmitting optical beams from the ranging subsystem 46 and the alignment guidance subsystem: AIM 48.

Following the beam combiner 82, the laser pulse beam 66 continues through a Z-telescope 84, which is operable to scan focus position of the laser pulse beam 66 in the patient's eye 43 along the Z axis. For example, the Z-telescope 84 can include a Galilean telescope with two lens groups (each lens group includes one or more lenses). One of the lens groups moves along the Z axis about the collimation position of the Z-telescope 84. In this way, the focus position of the spot in the patient's eye 43 moves along the Z axis. In general, there is a relationship between the motion of lens group and the motion of the focus point. For example, the Z-telescope can have an approximate 2× beam expansion ratio and close to a 1:1 relationship of the movement of the lens group to the movement of the focus point. The exact relationship between the motion of the lens and the motion of the focus in the Z axis of the eye coordinate system does not have to be a fixed linear relationship. The motion can be nonlinear and directed via a model or a calibration from measurement or a combination of both. Alternatively, the other lens group can be moved along the Z axis to adjust the position of the focus point along the Z axis. The Z-telescope 84 functions as a Z-scan device for scanning the focus point of the laser-pulse beam 66 in the patient's eye 43. The Z-telescope 84 can be controlled automatically and dynamically by the control electronics 54 and selected to be independent or to interplay with the X- and Y-scan devices described next.

After passing through the Z-telescope 84, the laser pulse beam 66 is incident upon an X-scan device 86, which is operable to scan the laser pulse beam 66 in the X direction, which is dominantly transverse to the Z axis and transverse to the direction of propagation of the laser pulse beam 66. The X-scan device 86 is controlled by the control electronics 54, and can include suitable components, such as a motor, galvanometer, or any other well-known optic moving device. The relationship of the motion of the beam as a function of the motion of the X actuator does not have to be fixed or linear. Modeling or calibrated measurement of the relationship or a combination of both can be determined and used to direct the location of the beam.

After being directed by the X-scan device 86, the laser pulse beam 66 is incident upon a Y-scan device 88, which is operable to scan the laser pulse beam 66 in the Y direction, which is dominantly transverse to the X and Z axes. The Y-scan device 88 is controlled by the control electronics 54, and can include suitable components, such as a motor, galvanometer, or any other well-known optic moving device. The relationship of the motion of the beam as a function of the motion of the Y actuator does not have to be fixed or linear. Modeling or calibrated measurement of the relationship or a combination of both can be determined and used to direct the location of the beam. Alternatively, the functionality of the X-scan device 86 and the Y-scan device 88 can be provided by an XY-scan device configured to scan the laser pulse beam 66 in two dimensions transverse to the Z axis and the propagation direction of the laser pulse beam 66. The X-scan and Y-scan devices 86, 88 change the resulting direction of the laser pulse beam 66, causing lateral displacements of UF focus point located in the patient's eye 43.

After being directed by the Y-scan device 88, the laser pulse beam 66 passes through a beam combiner 90. The beam combiner 90 is configured to transmit the laser pulse beam 66 while reflecting optical beams to and from a video subsystem 92 of the alignment guidance subsystem 48.

After passing through the beam combiner 90, the laser pulse beam 66 passes through an objective lens assembly 94. The objective lens assembly 94 can include one or more lenses. In many embodiments, the objective lens assembly 94 includes multiple lenses. The complexity of the objective lens assembly 94 may be driven by the scan field size, the focused spot size, the degree of telecentricity, the available working distance on both the proximal and distal sides of objective lens assembly 94, as well as the amount of aberration control.

After passing through the objective lens assembly 94, the laser pulse beam 66 passes through the patient interface 52. As described above, in many embodiments, the patient interface 52 includes a patient interface lens 96 having a posterior surface that is displaced vertically from the anterior surface of the patient's cornea and a region of a suitable liquid (e.g., a sterile buffered saline solution (BSS) such as Alcon BSS (Alcon Part Number 351-55005-1) or equivalent) is disposed between and in contact with the posterior surface of the patient interface lens 96 and the patient's cornea and forms part of an optical transmission path between the shared optics 50 and the patient's eye 43.

The shared optics 50 under the control of the control electronics 54 can automatically generate aiming, ranging, and treatment scan patterns. Such patterns can be comprised of a single spot of light, multiple spots of light, a continuous pattern of light, multiple continuous patterns of light, and/or any combination of these. In addition, the aiming pattern (using the aim beam 108 described below) need not be identical to the treatment pattern (using the laser pulse beam 66), but can optionally be used to designate the boundaries of the treatment pattern to provide verification that the laser pulse beam 66 will be delivered only within the desired target area for patient safety. This can be done, for example, by having the aiming pattern provide an outline of the intended treatment pattern. This way the spatial extent of the treatment pattern can be made known to the user, if not the exact locations of the individual spots themselves, and the scanning thus optimized for speed, efficiency, and/or accuracy. The aiming pattern can also be made to be perceived as blinking in order to further enhance its visibility to the user. Likewise, the ranging beam 102 need not be identical to the treatment beam or pattern. The ranging beam needs only to be sufficient enough to identify targeted surfaces. These surfaces can include the cornea and the anterior and posterior surfaces of the lens and may be considered spheres with a single radius of curvature. Also the optics shared by the alignment guidance: video subsystem does not have to be identical to those shared by the treatment beam. The positioning and character of the laser pulse beam 66 and/or the scan pattern the laser pulse beam 66 forms on the eye 43 may be further controlled by use of an input device such as a joystick, or any other appropriate user input device (e.g., control panel/GUI 56) to position the patient and/or the optical system.

The control electronics 54 can be configured to target the targeted structures in the eye 43 and ensure that the laser pulse beam 66 will be focused where appropriate and not unintentionally damage non-targeted tissue. Imaging modalities and techniques described herein, such as those mentioned above, or ultrasound may be used to determine the location and measure the thickness of the lens and lens capsule to provide greater precision to the laser focusing methods, including 2D and 3D patterning. Laser focusing may also be accomplished by using one or more methods including direct observation of an aiming beam, or other known ophthalmic or medical imaging modalities, such as those mentioned above, and/or combinations thereof. Additionally the ranging subsystem such as an OCT can be used to detect features or aspects involved with the patient interface. Features can include fiducials placed on the docking structures and optical structures of the disposable lens such as the location of the anterior and posterior surfaces.

In the embodiment of FIG. 3, the ranging subsystem 46 includes an OCT imaging device. Additionally or alternatively, imaging modalities other than OCT imaging can be used. An OCT scan of the eye can be used to measure the spatial disposition (e.g., three dimensional coordinates such as X, Y, and Z of points on boundaries) of structures of interest in the patient's eye 43. Such structure of interest can include, for example, the anterior surface of the cornea, the posterior surface of the cornea, the anterior portion of the lens capsule, the posterior portion of the lens capsule, the anterior surface of the crystalline lens, the posterior surface of the crystalline lens, the iris, the pupil, and/or the limbus. The spatial disposition of the structures of interest and/or of suitable matching geometric modeling such as surfaces and curves can be generated and/or used by the control electronics 54 to program and control the subsequent laser-assisted surgical procedure. The spatial disposition of the structures of interest and/or of suitable matching geometric modeling can also be used to determine a wide variety of parameters related to the procedure such as, for example, the upper and lower axial limits of the focal planes used for cutting the lens capsule and segmentation of the lens cortex and nucleus, and the thickness of the lens capsule among others. Additionally the ranging subsystem such as an OCT can be used to detect features or aspects involved with the patient interface. Features can include fiducials placed on the docking structures and optical structures of the disposable lens such as the location of the anterior and posterior surfaces.

The ranging subsystem 46 in FIG. 3 includes an OCT light source and detection device 98. The OCT light source and detection device 98 includes a light source that generates and emits an OCT source beam with a suitable broad spectrum. For example, in many embodiments, the OCT light source and detection device 98 generates and emits the OCT source beam with a broad spectrum from 810 nm to 850 nm wavelength. The generated and emitted light is coupled to the device 98 by a single mode fiber optic connection.

The OCT source beam emitted from the OCT light source and detection device 98 is passed through a pickoff/combiner assembly 100, which divides the OCT source beam into a sample beam 102 and a reference portion 104. A significant portion of the sample beam 102 is transmitted through the shared optics 50. A relative small portion of the sample beam is reflected from the patient interface 52 and/or the patient's eye 43 and travels back through the shared optics 50, back through the pickoff/combiner assembly 100 and into the OCT light source and detection device 98. The reference portion 104 is transmitted along a reference path 106 having an adjustable path length. The reference path 106 is configured to receive the reference portion 104 from the pickoff/combiner assembly 100, propagate the reference portion 104 over an adjustable path length, and then return the reference portion 106 back to the pickoff/combiner assembly 100, which then directs the returned reference portion 104 back to the OCT light source and detection device 98. The OCT light source and detection device 98 then directs the returning small portion of the sample beam 102 and the returning reference portion 104 into a detection assembly, which employs a time domain detection technique, a frequency detection technique, or a single point detection technique. For example, a frequency domain technique can be used with an OCT wavelength of 830 nm and bandwidth of 100 nm.

Once combined with the UF laser pulse beam 66 subsequent to the beam combiner 82, the OCT sample beam 102 follows a shared path with the UF laser pulse beam 66 through the shared optics 50 and the patient interface 52. In this way, the OCT sample beam 102 is generally indicative of the location of the UF laser pulse beam 66. Similar to the UF laser beam, the OCT sample beam 102 passes through the Z-telescope 84, is redirected by the X-scan device 86 and by the Y-scan device 88, passes through the objective lens assembly 94 and the patient interface 52, and on into the eye 43. Reflections and scatter off of structures within the eye provide return beams that retrace back through the patient interface 52, back through the shared optics 50, back through the pickoff/combiner assembly 100, and back into the OCT light source and detection device 98. The returning back reflections of the sample beam 102 are combined with the returning reference portion 104 and directed into the detector portion of the OCT light source and detection device 98, which generates OCT signals in response to the combined returning beams. The generated OCT signals that are in turn interpreted by the control electronics to determine the spatial disposition of the structures of interest in the patient's eye 43. The generated OCT signals can also be interpreted by the control electronics to measure the position and orientation of the patient interface 52, as well as to determine whether there is liquid disposed between the posterior surface of the patient interface lens 96 and the patient's eye 43.

The OCT light source and detection device 98 works on the principle of measuring differences in optical path length between the reference path 106 and the sample path. Therefore, different settings of the Z-telescope 84 to change the focus of the UF laser beam do not impact the length of the sample path for an axially stationary surface in the eye of patient interface volume because the optical path length does not change as a function of different settings of the Z-telescope 84. The ranging subsystem 46 has an inherent Z range that is related to the light source and detection scheme, and in the case of frequency domain detection the Z range is specifically related to the spectrometer, the wavelength, the bandwidth, and the length of the reference path 106. In the case of ranging subsystem 46 used in FIG. 3, the Z range is approximately 4-5 mm in an aqueous environment. Extending this range to at least 20-25 mm involves the adjustment of the path length of the reference path via a stage ZED 106 within ranging subsystem 46. Passing the OCT sample beam 102 through the Z-telescope 84, while not impacting the sample path length, allows for optimization of the OCT signal strength. This is accomplished by focusing the OCT sample beam 102 onto the targeted structure. The focused beam both increases the return reflected or scattered signal that can be transmitted through the single mode fiber and increases the spatial resolution due to the reduced extent of the focused beam. The changing of the focus of the sample OCT beam can be accomplished independently of changing the path length of the reference path 106.

Because of the fundamental differences in how the sample beam 102 (e.g., 810 nm to 850 nm wavelengths) and the UF laser pulse beam 66 (e.g., 1020 nm to 1050 nm wavelengths) propagate through the shared optics 50 and the patient interface 52 due to influences such as immersion index, refraction, and aberration, both chromatic and monochromatic, care must be taken in analyzing the OCT signal with respect to the UF laser pulse beam 66 focal location. A calibration or registration procedure as a function of X, Y, and Z can be conducted in order to match the OCT signal information to the UF laser pulse beam focus location and also to the relative to absolute dimensional quantities.

There are many suitable possibilities for the configuration of the OCT interferometer. For example, alternative suitable configurations include time and frequency domain approaches, single and dual beam methods, swept source, etc., are described in U.S. Pat. Nos. 5,748,898; 5,748,352; 5,459,570; 6,111,645; and 6,053,613.

The system 2 can be set to locate the anterior and posterior surfaces of the lens capsule and cornea and ensure that the UF laser pulse beam 66 will be focused on the lens capsule and cornea at all points of the desired opening. Imaging modalities and techniques described herein, such as for example, Optical Coherence Tomography (OCT), and such as Purkinje imaging, Scheimpflug imaging, confocal or nonlinear optical microscopy, fluorescence imaging, ultrasound, structured light, stereo imaging, or other known ophthalmic or medical imaging modalities and/or combinations thereof may be used to determine the shape, geometry, perimeter, boundaries, and/or 3-dimensional location of the lens and lens capsule and cornea to provide greater precision to the laser focusing methods, including 2D and 3D patterning. Laser focusing may also be accomplished using one or more methods including direct observation of an aiming beam, or other known ophthalmic or medical imaging modalities and combinations thereof, such as but not limited to those defined above.

Optical imaging of the cornea, anterior chamber, and lens can be performed using the same laser and/or the same scanner used to produce the patterns for cutting. Optical imaging can be used to provide information about the axial location and shape (and even thickness) of the anterior and posterior lens capsule, the boundaries of the cataract nucleus, as well as the depth of the anterior chamber and features of the cornea. This information may then be loaded into the laser 3-D scanning system or used to generate a three dimensional model/representation/image of the cornea, anterior chamber, and lens of the eye, and used to define the cutting patterns used in the surgical procedure.

Observation of an aim beam can also be used to assist in positioning the focus point of the UF laser pulse beam 66. Additionally, an aim beam visible to the unaided eye in lieu of the infrared OCT sample beam 102 and the UF laser pulse beam 66 can be helpful with alignment provided the aim beam accurately represents the infrared beam parameters. The alignment guidance subsystem 48 is included in the assembly 62 shown in FIG. 3. An aim beam 108 is generated by an aim beam light source 110, such as a laser diode in the 630-650 nm range.

Once the aim beam light source 110 generates the aim beam 108, the aim beam 108 is transmitted along an aim path 112 to the shared optics 50, where it is redirected by a beam combiner 114. After being redirected by the beam combiner 114, the aim beam 108 follows a shared path with the UF laser pulse beam 66 through the shared optics 50 and the patient interface 52. In this way, the aim beam 108 is indicative of the location of the UF laser pulse beam 66. The aim beam 108 passes through the Z-telescope 84, is redirected by the X-scan device 86 and by the Y-scan device 88, passes through the beam combiner 90, passes through the objective lens assembly 94 and the patient interface 52, and on into the patient's eye 43.

The video subsystem 92 is operable to obtain images of the patient interface and the patient's eye. The video subsystem 92 includes a camera 116, an illumination light source 118, and a beam combiner 120. The video subsystem 92 gathers images that can be used by the control electronics 54 for providing pattern centering about or within a predefined structure. The illumination light source 118 can be generally broadband and incoherent. For example, the light source 118 can include multiple LEDs. The wavelength of the illumination light source 118 is preferably in the range of 700 nm to 750 nm, but can be anything that is accommodated by the beam combiner 90, which combines the light from the illumination light source 118 with the beam path for the UF laser pulse beam 66, the OCT sample beam 102, and the aim beam 108 (beam combiner 90 reflects the video wavelengths while transmitting the OCT and UF wavelengths). The beam combiner 90 may partially transmit the aim beam 108 wavelength so that the aim beam 108 can be visible to the camera 116. An optional polarization element can be disposed in front of the illumination light source 118 and used to optimize signal. The optional polarization element can be, for example, a linear polarizer, a quarter wave plate, a half-wave plate or any combination. An additional optional analyzer can be placed in front of the camera. The polarizer analyzer combination can be crossed linear polarizers thereby eliminating specular reflections from unwanted surfaces such as the objective lens surfaces while allowing passage of scattered light from targeted surfaces such as the intended structures of the eye. The illumination may also be in a dark-field configuration such that the illumination sources are directed to the independent surfaces outside the capture numerical aperture of the image portion of the video system. Alternatively the illumination may also be in a bright field configuration. In both the dark and bright field configurations, the illumination light source maybe be used as a fixation beam for the patient. The illumination may also be used to illuminate the patient's pupil to enhance the pupil iris boundary to facilitate iris detection and eye tracking. A false color image generated by the near infrared wavelength or a bandwidth thereof may be acceptable.

The illumination light from the illumination light source 118 is transmitted through the beam combiner 120 to the beam combiner 90. From the beam combiner 90, the illumination light is directed towards the patient's eye 43 through the objective lens assembly 94 and through the patient interface 94. The illumination light reflected and scattered off of various structures of the eye 43 and patient interface travel back through the patient interface 94, back through the objective lens assembly 94, and back to the beam combiner 90. At the beam combiner 90, the returning light is directed back to the beam combiner 120 where the returning light is redirected toward the camera 116. The beam combiner can be a cube, plate, or pellicle element. It may also be in the form of a spider mirror whereby the illumination transmits past the outer extent of the mirror while the image path reflects off the inner reflecting surface of the mirror. Alternatively, the beam combiner could be in the form of a scraper mirror where the illumination is transmitted through a hole while the image path reflects off of the mirrors reflecting surface that lies outside the hole. The camera 116 can be an suitable imaging device, for example but not limited to, any silicon based detector array of the appropriately sized format. A video lens forms an image onto the camera's detector array while optical elements provide polarization control and wavelength filtering respectively. An aperture or iris provides control of imaging NA and therefore depth of focus and depth of field and resolution. A small aperture provides the advantage of large depth of field that aids in the patient docking procedure. Alternatively, the illumination and camera paths can be switched. Furthermore, the aim light source 110 can be made to emit infrared light that would not be directly visible, but could be captured and displayed using the video subsystem 92.

In many embodiments, the laser eye surgery system 2 is configured to be capable of delivering laser pulses to tightly focused points to disrupt and thereby incise tissue throughout a desired treatment volume within the eye 43.

FIG. 3 shows a mapped treatment region of the eye comprising the cornea 248, the posterior capsule 250, and the limbus. In particular, FIG. 3 is a diagram illustrating a predicted treatment volume 242 (hatched area) within which the laser eye surgery system 2 is capable of incising tissue. The predicted treatment volume 242 is bounded in the transverse directions by an x-direction boundary 244 and a y-direction boundary 246. Boundary conditions are determined by optical model simulation of threshold levels taking into account numerical aperture, aberration control, beam quality of the laser, polarization of the laser, pulse width, and optical train transmission anchored to empirically determined levels of tissue breakdown. To ensure that there is cutting, the boundaries factor in a margin above this threshold. A 2 times or 4 times margin above an empirically determined threshold is reasonable given the range of variation that goes into determining threshold levels. The predicted treatment volume 242 is wider in the x direction for z values (axial distance from the posterior surface of the patient interface lens 96) of less than about 7.25 mm and is wider in the y direction for z values of greater than about 7.25 mm. As shown, the predicted treatment volume 242 encompasses the cornea 248 and lens capsule 250 of the eye 43, thereby enabling the creation of incisions at any desired location in the cornea 248 and lens capsule 250.

The treatment region can be mapped with computer modeling, for example ray tracing and phased based optical modeling to incorporate factors such as laser beam quality, pulse width, system transmission, numerical aperture, polarization, aberration correction, and alignment. The treatment volume is shown extending along the Z-axis from the posterior surface of the optically transmissive structure of the patient interface a distance of over 15 mm, such that the treatment volume includes the cornea 248, and the lens in which the treatment volume of the lens includes the anterior capsule, the posterior capsule, the nucleus and the cortex. The treatment volume extends laterally from the center of the cornea 248 to beyond the limbus. The lateral dimensions of the volume are defined by a Y contour anterior to the limbus and by an X contour posterior to the limbus. The treatment volume shown can be determined by a person of ordinary skill in the art based on the teachings described herein. The lateral positions of predicted optical breakdown for ZL fixed to 30 mm and ZL fixed to 20 mm are shown. These surfaces that extend transverse to the axis 99 along the Z-dimension correspond to locations of optical scanning of the X and Y galvos to provide optical breakdown at lateral locations away from the axis 99. The curved non-planner shape of the scan path of optical breakdown for ZL-30 mm and ZL-20 mm can be corrected with the mapping and look up tables as described herein. The curved shape of the focus can be referred to as a warping of the optical breakdown depth and the look up tables can be warped oppositely or otherwise adjusted so as to compensate for the warping of the treatment depth, for example. Additionally, the warping inherent in the prediction from the model can be incorporated in the generic look-up table and any further error from this predicted form as indicated by measurement and application of a correction factor to offset this error may also be called a warping of the look up table.

The treatment region is shown for setting the laser beam energy about four times the threshold amount for optical breakdown empirically determined for a beam near the limbus of the system. The increased energy or margin above ensures that the beam system will be able to treat given variability in contributing factors. Theses contributing factors may include degradation over lifetime of the laser with regard to energy, beam quality, transmission of the system, and alignment.

The placement of the posterior surface of the optically transmissive structure of the patient interface away from the surface of the cornea can provide the extended treatment range as shown, and in many embodiments the optically transmissive structure comprises the lens. In alternative embodiments, the posterior surface of the optically transmissive structure can be placed on the cornea, for example, and the mapping and look up tables as described herein can be used to provide the patient treatment with improved accuracy.

The optically transmissive structure of the patient interface may comprise one or more of many known optically transmissive materials used to manufactures lenses, plates and wedges, for example one or more of glass, BK-7, plastic, acrylic, silica or fused silica for example.

The computer mapping of the treatment volume may optionally be adjusted with mapping based on measurements of a constructed system as described herein.

Figure 4A:
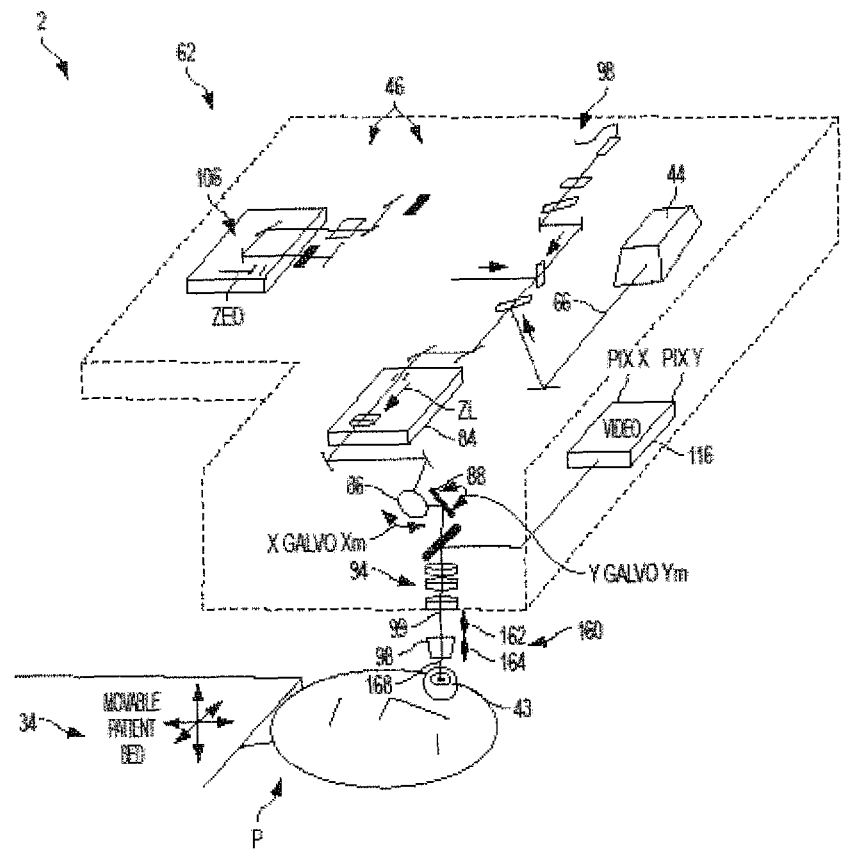
FIG. 4A shows correspondence among movable and sensor components of the laser delivery system, in accordance with many embodiments.

FIG. 4A shows correspondence among movable and sensor components of the laser delivery system 2. The movable components may comprise one or more components of the laser delivery system 2 as described herein. The movable components of the laser delivery system may comprise the zoom lens capable of moving distance ZL, the X galvo mirror 96 capable of moving an angular amount Xm, and the Y galvo mirror 88 capable of moving an angular amount Ym. The movable components of the OCT system may comprise the movable OCT reference arm configured to move the reference path 106 a distance ZED. The sensor components of the laser system may comprise the video camera having X and Y pixels, Pix X and Pix Y, respectively, and sensor components of the OCT system such as the spectral domain detection as described herein. The patient support which may comprise a bed is movable in three dimensions so as to align the eye 43 of the patient P with laser system 2 and axis 99 of the system. The patient interface assembly comprises an optically transmissive structure which may comprise an interface lens 96, for example, configured to be aligned with system 2 and an axis of eye 43. The patient interface lens can be placed on the patient eye 43 for surgery, and the optically transmissive structure can be placed at a distance 162 from the objective lens 94. In many embodiments, the optically transmissive structure comprises lens 96 placed a contact lens optical distance 162 (hereinafter "CLopt"). The optically transmissive structure comprises a thickness 164, and the thickness 164 may comprise a thickness of the contact lens 96, for example. Although the optically transmissive structure comprising contact lens 96 may contact the eye 2, in many embodiments the contact lens 168 is separated from the cornea with gap 168 extending between the lens and the vertex of the cornea, such that the posterior surface of the contact lens 168 contacts a solution comprising saline or a viscoelastic solution, for example.

Figure 4B:
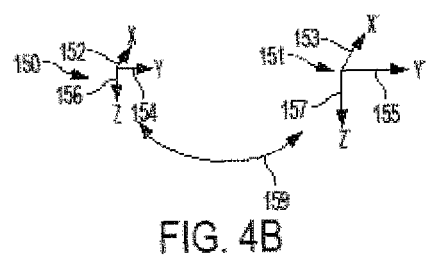
FIG. 4B shows mapping of coordinate references from an eye space coordinate reference system to a machine coordinate reference system, in accordance with many embodiments.

FIG. 4B shows mapping of coordinate references from an eye space coordinate reference system 150 to a machine coordinate reference system 151 so as to coordinate the machine components with the physical locations of the eye. The laser system 2 can map physical coordinates of the eye 43 to machine coordinates of the components as described herein. The eye space coordinate reference system 150 comprises a first X dimension 152, for example an X axis, a second Y dimension 154, for example a Y axis, and a third Z dimension 156, for example a Z axis, and the coordinate reference system of the eye may comprise one or more of many known coordinate systems such as polar, cylindrical or Cartesian, for example.

In many embodiments, the eye coordinate reference system corresponds to physical dimensions of the eye, which can be determined based on the tomography, video, and other measurements of the eye corrected with the refraction of the eye and the index of refraction of the eye as described herein, for example. For a targeted physical location of the eye having eye coordinate references based on the coordinate reference system 150, the processor can determine the machine coordinates of the machine coordinate reference system in one or more of many ways as described herein.

In many embodiments the reference system 150 comprises a right handed triple with the X axis oriented in a nasal temporal direction on the patient, the Y axis oriented superiorly on the patient and the Z axis oriented posteriorly on the patient. In many embodiments, the corresponding machine coordinate reference system 151 comprises a first X' dimension 153, a second Y' dimension 155, and a third Z' dimension 157 generally corresponding to machine actuators, and the coordinate reference system of the machine may comprise one or more of many known coordinate systems such as polar, cylindrical or Cartesian, and combinations thereof, for example.

The machine coordinate reference 151 may correspond to locations of one or more components of system 2. The machine coordinate reference system 151 may comprise a plurality of machine coordinate reference systems. The plurality of machine coordinate reference systems may comprise a coordinate reference system for each subsystem, for example. For example, dimension 157 may correspond to movement of the z-telescope lens capable of moving distance ZL. The dimension 153 may correspond to movement of the X galvo mirror 86 capable of moving an angular amount Xm, and the dimension 153 may correspond to movement of the Y galvo mirror 88 capable of moving an angular amount Ym. Alternatively or in combination, the dimension 157 may correspond to movable OCT reference arm configured to move the reference path 106 a distance ZED, along with dimension 157 corresponding to a movement of the z-telescope for the OCT beam, and the dimension 153 and the dimension 155 may correspond to movement of the X galvo mirror 86 and the Y galvo mirror 88, respectively, for the OCT beam. The dimension 151 may correspond to X pixels of the video camera and dimension 153 may correspond to Y pixels of the video camera. The axes of the machine coordinate reference system may be combined in one or more of many ways, for example the OCT reference arm movement of the reference path 106 the distance ZED can be combined with movement of the z-telescope lens capable of moving the distance ZL, for example. In many embodiments, the locations of the components of the laser system 2 are combined when in order to map the plurality of machine coordinate reference systems to the coordinate reference system 150 of eye 43.

In many embodiments, the eye coordinate reference system is mapped from an optical path length coordinate system to physical coordinates of the eye based on the index of refraction of the tissues of the eye. An example is the OCT ranging system where measurements are based on optical thicknesses. The physical distance can be obtained by dividing the optical path length by the index of refraction of the material through which the light beam passes. Preferable the group refractive index is used and takes into account the group velocity of the light with a center wavelength and bandwidth and dispersion characteristics of the beam train. When the beam has passed through more than one material, the physical distance can be determined based on the optical path length through each material, for example. The tissue structures of the eye and corresponding index of refraction can be identified and the physical locations of the tissue structures along the optical path determined based on the optical path length and the indices of refraction. When the optical path length extends along more than one tissue, the optical path length for each tissue can be determined and divided by the corresponding index of refraction so as to determine the physical distance through each tissue, and the distances along the optical path can be combined, for example with addition, so as to determine the physical location of a tissue structure along the optical path length. Additionally, optical train characteristics may be taken into account. As the OCT beam is scanned in the X and Y directions and departure from the telecentric condition occurs due to the axial location of the galvo mirrors, a distortion of the optical path length is realized. This is commonly known as fan error and can be corrected for either through modeling or measurement.

As one or more optical components and light sources as described herein may have different path lengths, wavelengths, and spectral bandwidths, in many embodiments the group index of refraction used depends on the material and the wavelength and spectral bandwidth of the light beam. In many embodiments, the index of refraction along the optical path may change with material. For example, the saline solution may comprise a first index of refraction, the cornea may comprise a second index of refraction, the anterior chamber of the eye may comprise a third index of refraction, and the eye may comprise gradient index lens having a plurality of indices of refraction. While optical path length through these materials is governed by the group index of refraction, refraction or bending of the beam is governed by the phase index of the material. Both the phase and group index can be taken into account to accurately determine the X, Y, and Z location of a structure. While the index of refraction of tissue such as eye 43 can vary with wavelength as described herein, approximate values include: aqueous humor 1.33; cornea 1.38; vitreous humor 1.34; and lens 1.36 to 1.41, in which the index of the lens can differ for the capsule, the cortex and the nucleus, for example. The phase index of refraction of water and saline can be about 1.325 for the ultrafast laser at 1030 nm and about 1.328 for the OCT system at 830 nm. The group refractive index of 1.339 differs on the order of 1% for the OCT beam wavelength and spectral bandwidth. A person of ordinary skill in the art can determine the indices of refraction and group indices of refraction of the tissues of the eye for the wavelengths of the measurement and treatment systems as described herein. The index of refraction of the other components of the system can be readily determined by a person of ordinary skill in the art based on the teachings described herein.

Figure 5A:
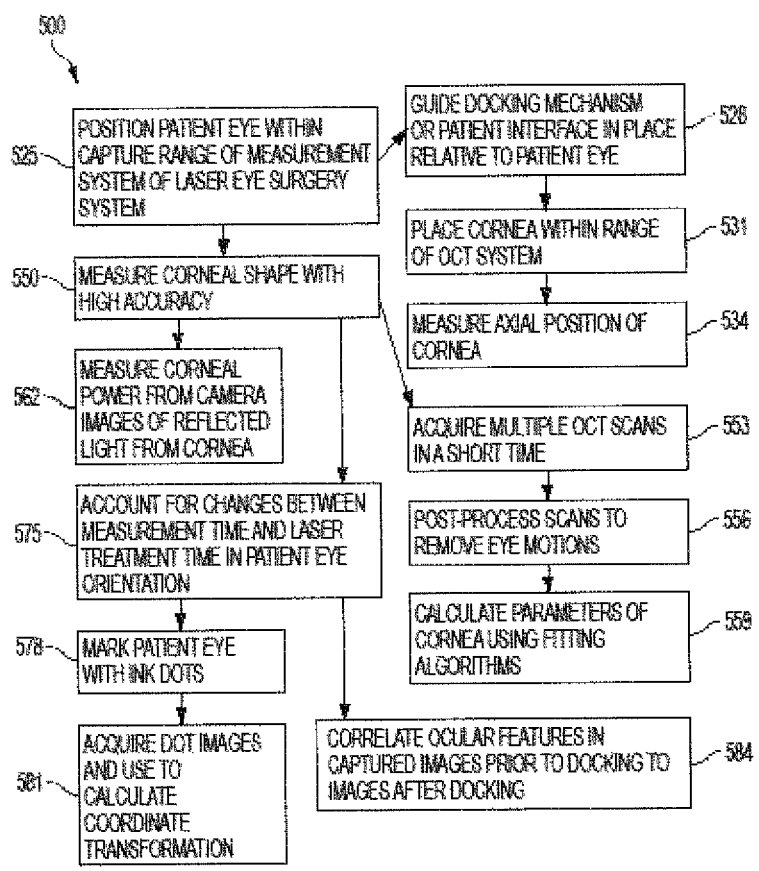
FIG. 5A shows a flow chart of a method for mapping the eye, in accordance with many embodiments.

FIG. 5A shows a flow chart of a method 500 for providing accurate and distortion-free corneal topography measurement and subsequent integration with the laser treatment, in accordance with embodiments. The method 500 comprises the following main steps. In a step 525, the patient's eye is positioned within the capture range of the measurement system of the laser eye surgery system 2 described herein. In a step 550, the measurement system is used to measure corneal shape with high accuracy. Such a measurement system may comprise the ranging subsystem 46 described above. In a step 575, any changes in the patient eye orientation that may occur between the measurement time and the laser treatment time is accounted for.

Positioning step 525: In the step 525, the patient's eye is positioned within the capture range of the measurement system of the laser eye surgery system as described herein. Positioning of the patient for laser surgery is typically enabled by motion of the patient bed 34 or by motion of the laser system 2. Typically, the operator has manual control of the lateral and axial position, guiding the docking mechanism or patient interface 52 into place in a step 528. In the absence of a docking mechanism, an operator means for guiding the motion so that the eye, and specifically the cornea, is placed within the operative range of the measurement system may be provided. This can be accomplished with the use of subsystems of the laser system 2 described herein such as alignment guidance system 48 of laser system 2. Initial patient position can be guided by a video camera, guiding the eye into lateral position by centering the video image, and into axial position by focusing the image. At this point, the cornea is placed within the capture range of the OCT system of the ranging subsystem 46 or imaging subsystem 546, typically X mm to Y mm axially, in a step 531. The OCT system can be used to measure the axial position of the cornea in a step 534, and a suitable display provides the operator guidance for final, accurate positioning. Alternatively, a visual imaging system such as a camera, a camera coupled to a microscope which may share optics with the laser system 2, a CCD, among others may be used instead of the OCT system to facilitate the positioning step 525.

Since the video and OCT systems are typically configured to operate with the docking system, which often has additional optical elements and liquid medium in the optics path, the focusing algorithms of the laser system may be adjusted to account for operation without the docking mechanism optics and interface medium.

Measurement step 550: In the step 550, the measurement system is used to measure corneal shape with high accuracy. The laser system 2 comprises a subsystem for mapping the ocular surfaces that are being treated such as the ranging subsystem 46 having an OCT system described herein or the imaging subsystem 546. As described below, the imaging subsystem 546 may apply other modalities for mapping the ocular surfaces such as Placido imaging, Hartmann-shack wavefront sensing, confocal tomography, low coherence reflectometry, among others. The measurement step 550 can be performed once the eye is positioned correctly in the step 525 above. A fixation light can optionally be introduced to help the patient keep the eye pointed at a fixed angle. If the measurement data capture is sufficiently fast, for example, on the order of one second, a fixation light may not be necessary. In a step 553 of measurement 550, multiple OCT or other scans of the cornea surfaces can be acquired in a short time. Multiple scans can increase the confidence of obtaining good data. In a step 556, post-processing of the scans can remove potential eye motion and further improve the measurement accuracy. In a step 562 of measurement step 550, corneal power can be measured from camera images of reflected light from the cornea.

Once the cornea surfaces have been mapped, polynomial, or other fitting algorithms can be used to calculate commonly used parameters of the cornea in a step 559. Commonly used parameters include the optical power of the cornea, astigmatic axis angle, and astigmatism magnitude.

Coordinate system transfer step 575: In the step 575, any changes in the patient eye orientation that may occur between the measurement time and the laser treatment time is accounted for. Often times, it is probable that when the patient eye is docked for treatment such as with the suction ring of the patient interface 52, the eye, including its various anatomical features, will change its position relative to the laser system coordinates. This change can be a result of patient head movement, eye movement, or because of force applied during docking. In some cases, the refractive properties of the air or any liquid over the eye can distort the images of the eye. For example, the suction ring of the patient interface 52 may be filled with one or more of a solution, saline, or a viscoelastic fluid. It can be helpful to transform the corneal measurements, like the astigmatic axis angle, to a new coordinate system to account for any movement and distortion. Several means for accomplishing this are provided.

In some embodiments, the operator can mark the patient eye prior to the measurement with ink dots that are typically positioned diametrically across on the periphery of the cornea in a step 578. These dots can be acquired by the imaging camera after docking for treatment and used for calculating the coordinate transformation in a step 581.

In other embodiments, ocular features that are visible in the video images, or the OCT or other scans, taken during the measurement step are used. These features are correlated to the images taken after docking for treatment in a step 584. This correlation can be done by digital image processing algorithms, or manually by the operator. When done manually, the operator is presented by overlapped images (measurement and treatment steps) on the control screen, and the images are manually manipulated in translation and rotation until they are visibly matched. The image manipulation data can be detected by the display software and used for the coordinate transform.

Although the above steps show method 500 of providing accurate and distortion-free corneal topography measurement and subsequent integration with the laser treatment in accordance with many embodiments, a person of ordinary skill in the art will recognize many variations based on the teaching described herein. The steps may be completed in a different order. Steps may be added or deleted. For example, the shape of the cornea may be measures before, during, or after docking for treatment such as with a suction ring of the patient interface 52. Many of the steps may be repeated as often as beneficial to the method.

One or more of the steps of the method 500 may be performed with the circuitry as described herein, for example, one or more the processor or logic circuitry such as the programmable array logic for field programmable gate arrays. The circuitry may be programmed to provide one or more of the steps of method 500, and the program may comprise program instructions stored on a computer readable memory or programmed steps of the logic circuitry such as the programmable array logic or the field programmable gate array, for example.

Figure 5B:
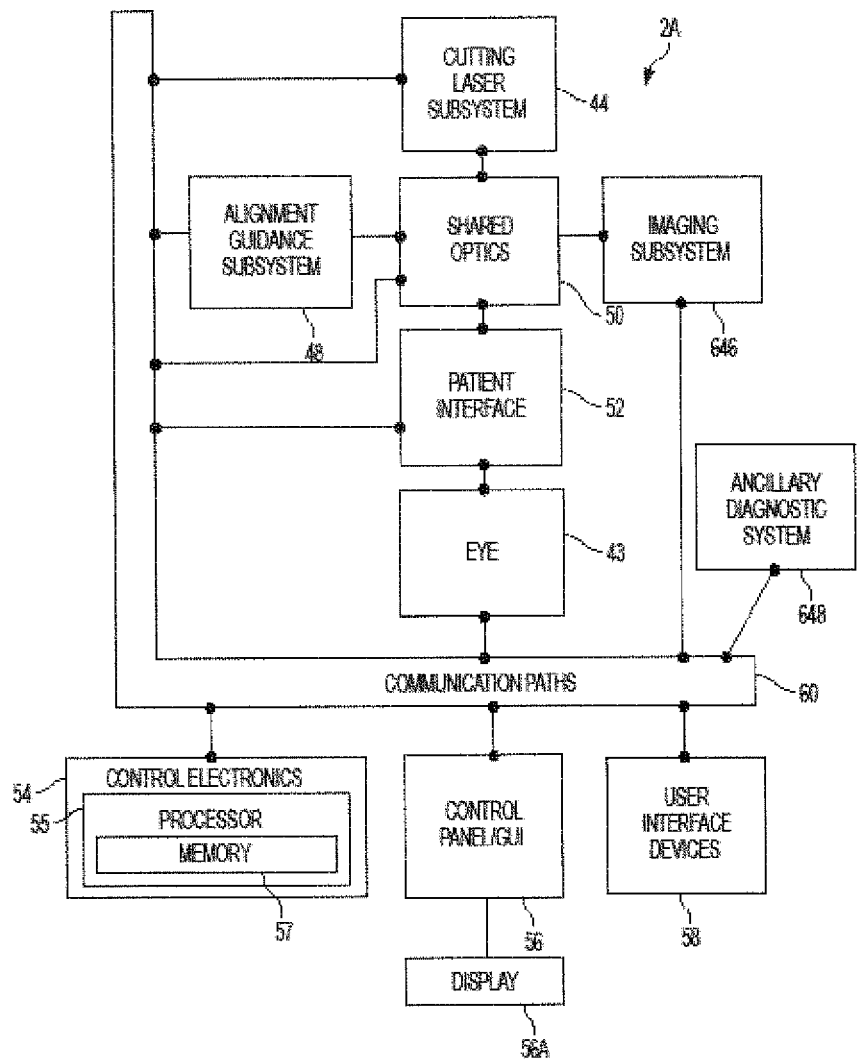
FIG. 5B shows a simplified block diagram showing a top level view of the configuration of a laser eye surgery system which can perform the method of FIG. 5A, in accordance with many embodiments.

FIG. 5B shows a laser eye surgery 2 in accordance with embodiments. The laser eye surgery system 2 is similar to the laser eye surgery system 2 as described herein and comprises many of the same components. In particular, the laser eye surgery system 2A comprises an imaging subsystem 646 which may be used to visualize and image the eye 43, and the control panel/GUI 56 comprises a display 56A. The laser eye surgery system 2A may be configured to couple to a separate and distinct ancillary diagnostic system 648. For the laser eye surgery system 2, the OCT system of the ranging subsystem 46 may be used to position the patient eye in the step 525 and/or to measure the shape of the cornea in the step 550. For the laser eye surgery system 2A, the ancillary diagnostic system 648 is used to measure the shape of the cornea in the step 550. The ancillary diagnostic system 648 may apply any number of modalities to measure the shape of the eye including one or more of a keratometry reading of the eye, a corneal topography of the eye, an optical coherence tomography of the eye, a Placido disc topography of the eye, a reflection of a plurality of points from the cornea topography of the eye, a grid reflected from the cornea of the eye topography, a Hartmann-Shack topography of the eye, a Scheimpflug image topography of the eye, a confocal tomography of the eye, or a low coherence reflectometry of the eye. The shape of the cornea can be measured before, during, or after the patient interface 52 is docked with the eye of the patient. The shape of the cornea may be measured using the ancillary diagnostic system 648 while the ancillary diagnostic system 648 is separate from the laser eye surgery system 2A, such as by being in a different room. Images captured by the ranging subsystem 46 of the laser eye surgery system 2 or the imaging subsystem 546 of the laser eye surgery system 2A and the ancillary diagnostic system 548 may be displayed with a display of the control panel/GUI 56 of the laser eye surgery system 2 or the display 56A of the laser eye surgery system 2A, respectively. The control panel/GUI 56 may also be used to modify, distort, or transform any of the displayed images.

Figure 6A:
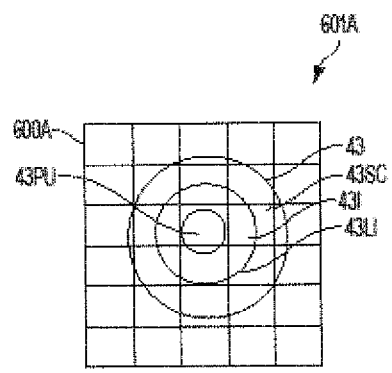
FIG. 6A shows a coordinate system overlaid on an image of the eye, in accordance with many embodiments.
Figure 6B:
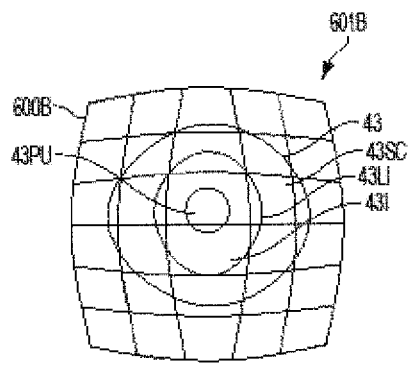
FIG. 6B shows a distorted coordinate system overlaid on the eye image of FIG. 6A to account for distortions due coupling of the eye to a patient interface, in accordance with many embodiments.
Figure 6C:
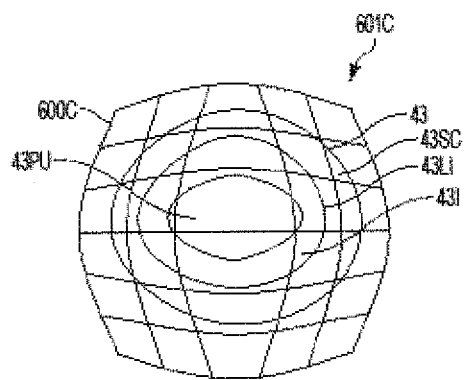
FIG. 6C shows a distorted coordinate system overlaid on the eye image of FIG. 6B to account for distortion due coupling of the eye to a patient interface as well as liquid in the patient interface disposed over the eye, in accordance with many embodiments.

FIGS. 6A to 6C show images of the eye which may be displayed for example in the display 56A of the laser eye surgery system 2A or the display of the laser eye surgery system 2, for example. The images shown illustrate distortion which may occur and the distortion may not be to scale and is provided for illustration purposes in accordance with embodiments.

FIG. 6A shows a coordinate system 600A overlaid on an image 601A of an eye EY. The image 601A of the eye 43 shows various anatomical features including the sclera 43SC, the limbus 43LI, the iris 43I, and the pupil 43PU. Similar images and biometric information can be obtained with similar maps. In many embodiments, this image 601A can be captured by the imaging subsystem 546 of the laser eye surgery system 2A. The image 601A is captured prior to coupling the eye with a suction ring of the patient interface 52 of the laser eye surgery system 2. The image 601A may most accurately represent the positions of the various tissue structures of the eye 43. The image 601A may comprise one or more of many images or measurements as described herein. A person of ordinary skill in the art will recognize that the pupil seen through the cornea/air interface comprises a virtual pupil of the eye. Although the shape and optical power of the cornea may provide distortion and magnification of the pupil and iris, a person of ordinary skill in the art can correct this distortion and magnification based on the teaching described herein and in accordance with embodiments as appropriate. For example, the virtual image of the pupil can be transformed to an eye space coordinate system 150 as described herein.

The structures shown in coordinate system 600A can be transformed to the coordinate reference system 150 of eye 2 in one or more of many ways. For example, the tissue structures shown in the image such as the limbus and the iris can be identified, and the transform to the eye coordinate reference system 150 determined based on the location of the tissue structure and depth and location in relation to correspondence optical tissue surfaces such as the surface of the cornea. The locations of the tissue structures identified in the image 601 can be determined and mapped to eye coordinate reference system 150 or to one or more coordinate reference systems as described herein.

In many embodiments, iris registration is used to determine a cyclotorsional angle of the eye. A first image of the iris can be obtained with a first camera prior to the patient interface contacting the eye, and a second image of the iris can be obtained when the patient interface contacts the eye. The first camera image of the iris can be registered with the second camera image of the iris of the patient in order to determine the cyclo torsional angle of the eye as described herein. In many embodiments, the first non-contact image of the eye comprises an image of the iris wherein the cornea of the eye magnifies and may distort the virtual image of the iris seen with the camera, and the second contact image of the eye comprises an image of the eye measured when the patient interface contacts the eye. The first image and the second image can be registered in one or more of many ways, and the processor can be configured with instructions to determine the cyclotorsional angle of the eye with instructions of an algorithm such as one or more of an image matching algorithm or a pattern recognition algorithm, for example. The processor comprising the instructions of the algorithm can be configured to identify a pattern of the first image in relation to an axis of the eye as described herein and to identify the location of the pattern in the second image in order to determine the cyclotorsional angle of the eye, for example.

In many embodiments, ray tracing through the full thickness corneal profile map can be used to correct distortions of the cornea, such as one or more of distortions of the anterior corneal surface of the posterior corneal surface. For example, when the eye has been docked and the fluid of the patient interface contacts the eye, distortions of the posterior surface of the eye can influence light rays travelling through the cornea, and distortions of images of tissue structure posterior to the posterior surface of the cornea can be corrected in response to ray tracing. The ray tracing can be performed by a person of ordinary skill in the art using Snell's law and the index of refraction of the cornea and contacting material such as air, interface fluid, or aqueous humor, for example. Alternatively or in combination, distortions of the anterior corneal surface and the corresponding distortion of images measured through the cornea can be corrected with ray tracing, for example when the cornea is exposed to air. While distortions of the anterior corneal surface can be corrected in a manner similar to the posterior surface with ray tracing, work in relation to embodiments suggests that coupling the eye to the patient interface with a fluid contacting the patient interface and having an index of refraction similar to the cornea can decrease the effect of distortions of the anterior corneal surface. Based on the teachings disclosed herein, a person of ordinary skill in the art can determine and correct for distortions of images of the eye related to corneal distortions with ray tracing and corneal profile maps as described herein, for example.

In many embodiments one or more of the first image or the second image is adjusted in response to distortion of the one or more of the first image or the second image. The distortion can be related to the index of refraction viscous fluid into the patient interface that affects the optical properties of the image of the eye, or the distortion of the optical delivery system, and combinations thereof. In many embodiments, the distortion of the cornea can be determined in response to a thickness profile of the cornea, and aberrations of the image introduced by the thickness profile of the cornea corrected.

FIG. 6A1 shows corneal profile data 610A of cornea 43C for the coordinate system and image of FIG. 6A. The corneal profile data 610A comprises a plurality of corneal profiles from the tomography system taken with the patient interface away from the eye as in FIG. 6A. The plurality of corneal profiles comprises a first corneal profile 612A, a second corneal profile 614A and a third corneal profile 616A. Additional corneal profiles can be taken. The cornea profiles can be obtained with tomography scans along a plane for example, and detection of the corneal surface. The corneal surface can be fit as described herein, for example with polynomials as described herein. The fit corneal surface can be used to determine the corneal topography and treatment parameters as described herein. The corneal profile data may comprise coordinate system 600A, for example.

FIG. 6B shows a distorted coordinate system 600B overlaid on the eye image 601B of the eye 43. The image 601A of the eye 43 shows various anatomical features including the sclera 43SC, the limbus 43LI, the iris 431, and the pupil 43PU. In many embodiments, this image 601B is taken of the eye by a visual imaging system of the laser eye surgery system 2. This image 601B is taken when the anterior surface of the eye 43 is coupled with a suction ring of the laser eye surgery system 2 to expose the anterior surface to air. The suction ring may distort the tissue structures of the eye 43 when placed thereon. The locations of the various tissue structures of the eye, such as one or more structures of the iris, in relation to the distorted coordinate system 600B can be mapped to their respective locations the coordinate system 600A in image 601A to account for this distortion.

FIG. 6C shows a distorted coordinate system 600C overlaid on the eye image 601C of the eye 43. The image 601C of the eye 43 shows various anatomical features including the sclera 43SC, the limbus 43LI, the iris 431, and the pupil 43PU. In many embodiments, this image 601C is taken of the eye by a visual imaging system of the laser eye surgery system 2. This image 601C is taken when the anterior surface of the eye 43 is coupled with a suction ring of the laser eye surgery system 2 and the suction ring is filled with a liquid such as saline or viscoelastic substance. In addition to distortion from interfacing with the suction ring, the refractive properties of the liquid may also distort light reflecting back from the anterior surface of the eye EY. The locations of the various tissue structures of the eye, such as one or more structures of the iris, in relation to the distorted coordinate system 600C can be mapped to their respective locations the coordinate system 600A in image 601A to account for these distortions. Alternatively or in combination, the structures can be mapped to eye coordinate reference system 150.

FIG. 6C1 shows corneal profile data 610C of cornea CO for the coordinate system and image of FIG. 6C. The corneal profile data 610C can be provided with mapping of the corneal profile data 610A, or based on a second set of similar measurements. The corneal profile data 610C comprises a plurality of corneal profiles from the tomography system taken with the patient interface away from the eye as in FIG. 6A. The plurality of corneal profiles comprises a first corneal profile 612C, a second corneal profile 614C and a third corneal profile 616C. Additional corneal profiles can be taken. The cornea profiles can be obtained with tomography scans along a plane for example, and detection of the corneal surface. The corneal surface can be fit as described herein, for example with polynomials as described herein. The corneal profile data 610C may a coordinate system 600C overlaid. The corneal profile data 610C of coordinate system 600C may be mapped to eye coordinate reference 150 as described herein, for example. Alternatively or in combination, the corneal profile data 610C may comprise eye coordinate reference 150 as described herein, for example when the treatment is mapped based on the patient interface coupled to the eye.

In many embodiments, the non-distorted image 601A is modified to provide a distorted first image with a distortion similar to that in images 601B or 601C. The distorted image 601A may then be displayed on the display 56A or other display of the laser eye surgery system 2 or 2A. A user of the laser eye surgery system 2 or 2A can adjust one or more of a location or an angle of the distorted image 601A on the display 56A or other display. Locations of a plurality of laser beam pulses from the cutting laser subsystem 44 can then be adjusted in response to the location or the angle of the first distorted image 601A on the display 56A or other display. In some embodiments, the distorted first image 601A is overlaid on the distorted image 601B or 601C on the display 56A or other display to determine the position and the angle of the eye for treatment. A processor of the laser eye surgery system 2 or 2A can determine the position and the angle of the distorted first image 601A on the display in response to user input to adjust the locations of the plurality of laser beam pulses from the cutting laser subsystem 44.

FIG. 6A2 shows corneal thickness profile data for the coordinate system and images of FIGS. 6A and 6A1. The corneal profile data 610A comprises a plurality of corneal thickness profiles from the tomography system taken with the patient interface away from the eye as in FIG. 6A. The plurality of corneal profiles comprises a first corneal thickness profile 617A, a second corneal thickness profile 618A and a third corneal profile 619A. Additional corneal profiles can be taken.

Each of the thickness profiles may comprise a difference between an anterior surface profile and a posterior surface profile, for example. The first corneal thickness profile 617A may comprise a difference between a first anterior surface profile 612A and a first posterior surface profile 611A. The second corneal thickness profile 618A may comprise a difference between second anterior surface profile 614A and a second posterior surface profile 613A. A third corneal profile 619A may comprise a difference between third anterior surface profile 616A and a third posterior surface profile 615A. Additional corneal profiles can be taken.

Each of the corneal thickness profiles coordinate system 600AC of can be mapped to the physical eye coordinate reference system 150.

FIG. 6C2 shows corneal thickness profile data for the coordinate system and images of FIGS. 6C and 6C1. The corneal thickness profile data 610A comprises a plurality of corneal thickness profiles from the tomography system taken with the patient interface away from the eye as in FIG. 6C. The plurality of corneal profiles comprises a first corneal thickness profile 617C, a second corneal thickness profile 618C and a third corneal profile 619C. Additional corneal profiles can be taken.

Each of the thickness profiles may comprise a difference between an anterior surface profile and a posterior surface profile, for example. The first corneal thickness profile 617C may comprise a difference between a first anterior surface profile 612C and a first posterior surface profile 611C. The second corneal thickness profile 618C may comprise a difference between second anterior surface profile 614C and a second posterior surface profile 613C. A third corneal profile 619C may comprise a difference between third anterior surface profile 616C and a third posterior surface profile 615C. Additional corneal profiles can be taken.

Each of the corneal thickness profiles coordinate system 600C of can be mapped to the physical eye coordinate reference system 150.

FIG. 6A3 shows a corneal thickness profile map 620A for the coordinate system and images of FIGS. 6A, 6A1 and 6A2. The thickness profile map generally comprises a representation of three dimensional thickness profile data of the cornea, and may comprise three dimensional thickness data of the cornea. For example, the thickness profile data may comprise a two dimensional array in which the thickness of the cornea is stored for each two dimensional location of the array.

The corneal thickness profile map 620 can be determined based on the first corneal thickness profile 617A, the second corneal thickness profile 618A and the third corneal thickness profile 619A, for example. The corneal thickness profile map 620A can be shown in relation to the pupil 43PU and the limbus 43LI. The corneal thickness profile map 620A can be displayed to the user in one or more of many known formats such as with color coding of thicknesses or with equal depth contour lines. The equal depth contour lines may comprise a first equal depth contour line 622A, a second equal depth contour line 624A. The corneal thickness profile data can be fit as described herein, for example with a polynomial as described herein, in order to provide the corneal thickness profile map 620. The maps can be obtained with reference to coordinate system 600A and mapped to eye coordinate reference system 150, for example.

FIG. 6C3 shows a corneal thickness profile map 620C for the coordinate system and images of FIGS. 6C, 6C1 and 6C2. The corneal thickness profile map 620C can be determined based on the first corneal thickness profile 617C, the second corneal thickness profile 618C and the third corneal thickness profile 619C, for example. The corneal thickness profile map 620C can be shown in relation to the pupil 43PU and the limbus 43LI. The corneal thickness profile map 620C can be displayed to the user in one or more of many known formats such as with color coding of thicknesses or with equal depth contour lines. The equal depth contour lines may comprise a first equal depth contour line 622C, a second equal depth contour line 624C. The corneal thickness profile data can be fit as described herein, for example with a polynomial as described herein, in order to provide the corneal thickness profile map 620. The maps can be obtained with reference to coordinate system 600C and mapped to eye coordinate reference system 150, for example.

Work in relation to embodiments of the present disclosure suggest that the corneal thickness profile maps and data as disclosed herein are resistant to mechanical deformation when the suction ring is placed on the eye, and can be used to align the eye about the cyclotorsion al axis, for example. The corneal thickness profile maps can be particularly well suited to align eyes having prior refractive surgery, such as eyes that have received LASIK or PRK or other refractive surgery, for example.

Figure 7:
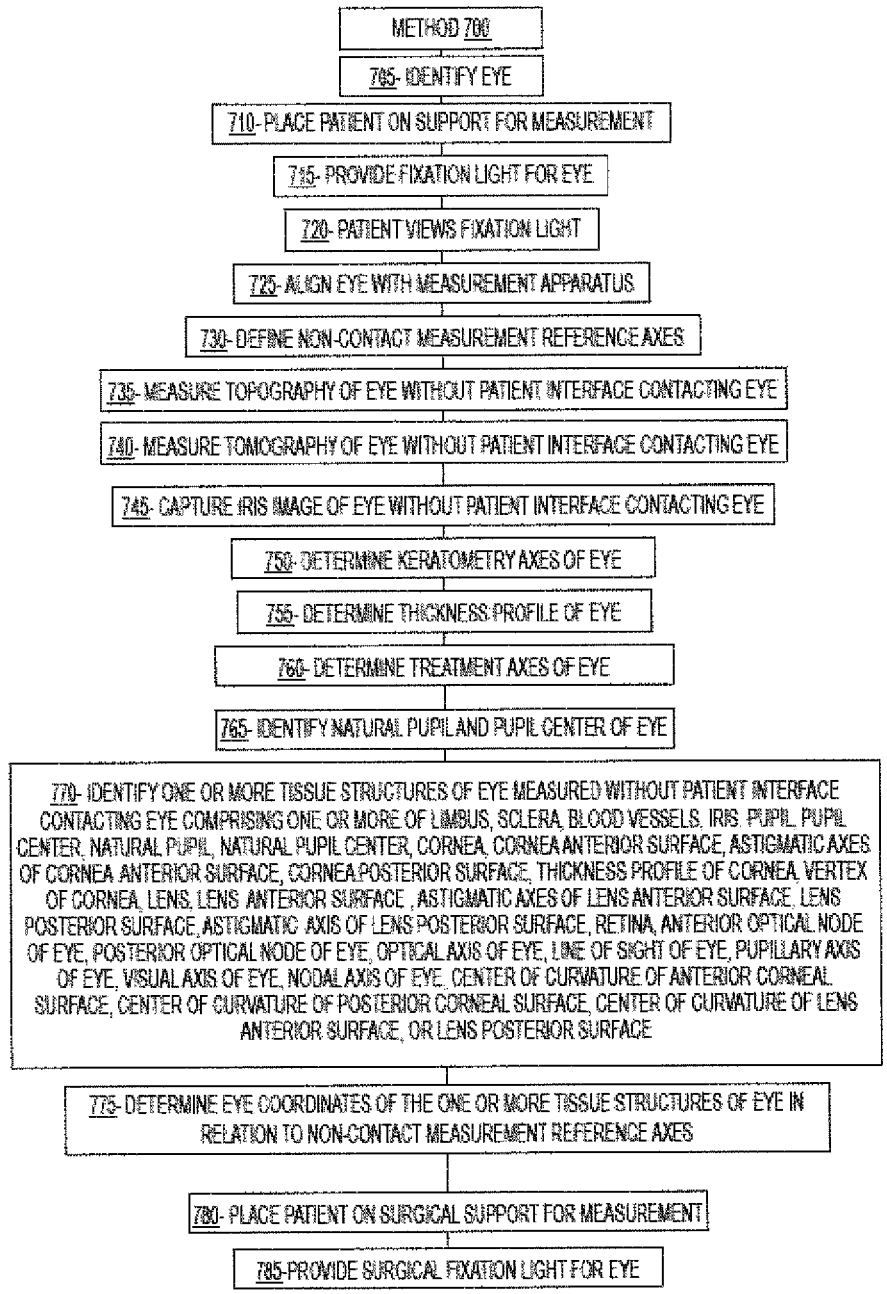
FIG. 7 shows a method of treating an eye with a laser beam, in accordance with embodiments.
Figure 7:
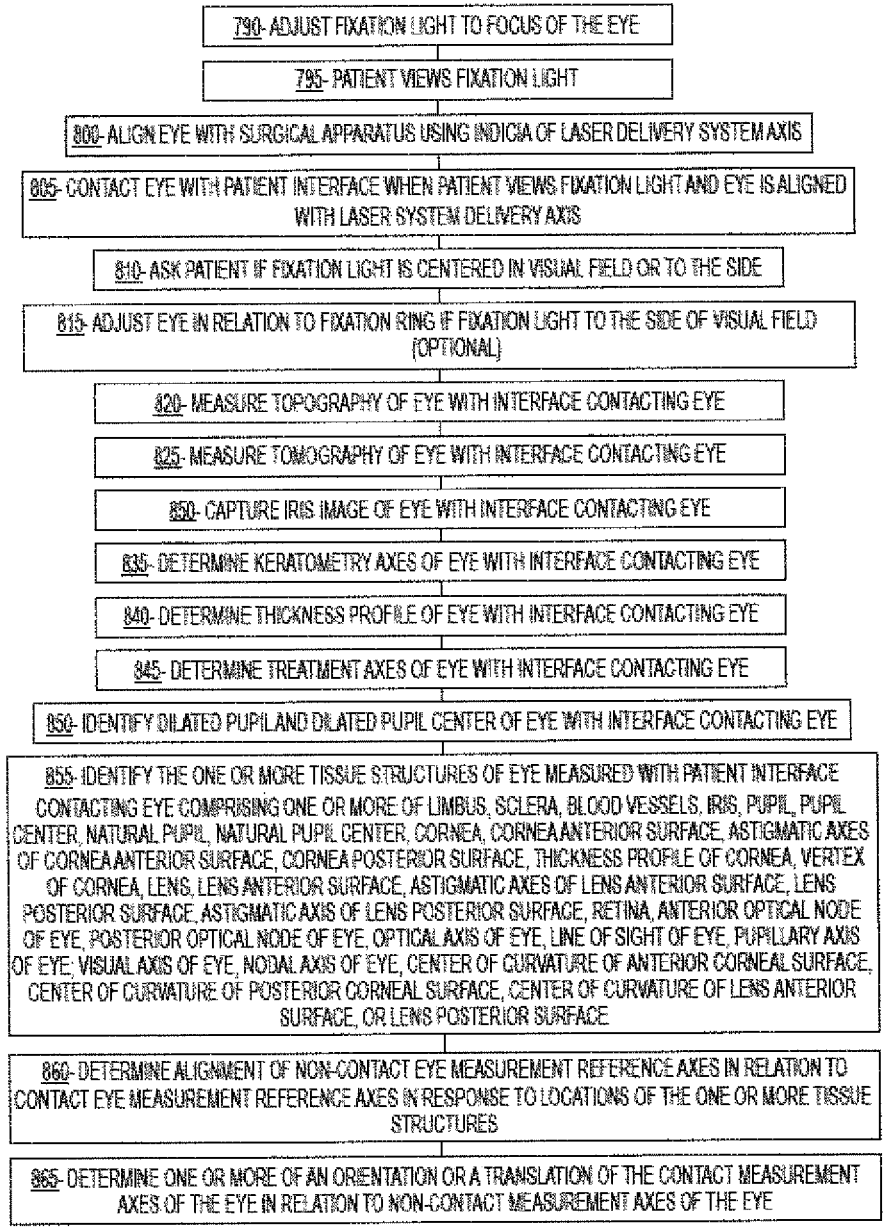
Figure 7:
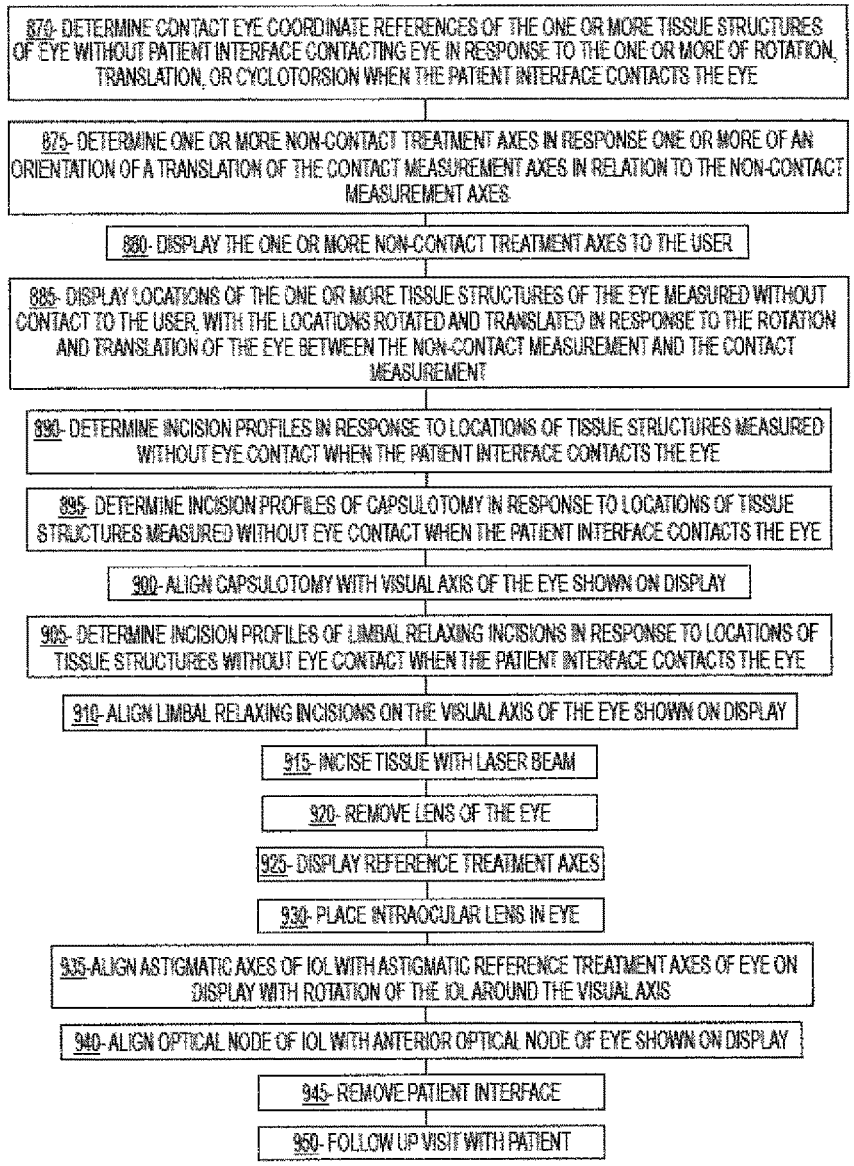

FIG. 7 shows a method 700 of treating an eye with a laser beam. Method 700, the steps of the method 700 comprise one or more of the following steps. At a step 705, the eye is identified. At a step 710, the patient is placed on the support for measurement. At a step 715, provide fixation light for eye. At a step 720, patient views fixation light. At a step 725, align eye with measurement apparatus. At a step 730, define non-contact measurement reference axes. At a step 735, measure topography of eye without patient interface contacting eye. At a step 740, measure tomography of eye without patient interface contacting eye. At a step 745, capture Iris image of eye without patient interface contacting eye. At a step 750, determine keratometry axes of eye. At a step 755, determine thickness profile of eye. At a step 760, determine treatment axes of eye. At a step 765, identify natural pupil and pupil center of eye. At a step 770, identify one or more tissue structures of eye measured without patient interface contacting eye comprising one or more of limbus, sclera, blood vessels, iris, pupil, pupil center, natural pupil, natural pupil center, cornea, cornea anterior surface, astigmatic axes of cornea anterior surface, cornea posterior surface, thickness profile of cornea, vertex of cornea, lens, lens anterior surface, astigmatic axes of lens anterior surface, lens posterior surface, astigmatic axis of lens posterior surface, retina, anterior optical node of eye, posterior optical node of eye, optical axis of eye, line of sight of eye, pupillary axis of eye, visual axis of eye, nodal axis of eye, center of curvature of anterior corneal surface, center of curvature of posterior corneal surface, center of curvature of lens anterior surface, or lens posterior surface. At a step 775, determine eye coordinates of the one or more tissue structures of eye in relation to non-contact measurement reference axes. At a step 780, place patient on surgical support for measurement. At a step 785, provide surgical fixation light for eye. At a step 790, adjust fixation light to focus of the eye. At a step 795, patient views fixation light.

At a step 800, align eye with surgical apparatus using indicia of laser delivery system axis. At a step 805, contact eye with patient interface when patient views fixation light and eye is aligned with laser system delivery axis. At a step 810, ask patient if fixation light is centered in visual field or to the side. At a step 815, adjust eye in relation to fixation ring if fixation light to the side of visual field. At a step 820, measure topography of eye with interface contacting eye. At a step 825, measure tomography of eye with interface contacting eye. At a step 830, capture Iris image of eye with interface contacting eye. At a step 835, determine keratometry axes of eye with interface contacting eye. At a step 840, determine thickness profile of eye with interface contacting eye. At a step 845, determine treatment axes of eye with interface contacting eye. At a step 850, identify dilated pupil and dilated pupil center of eye with interface contacting eye. At a step 855, identify the one or more tissue structures of eye measured with patient interface contacting eye comprising one or more of limbus, sclera, blood vessels, iris, pupil, pupil center, natural pupil, natural pupil center, cornea, cornea anterior surface, astigmatic axes of cornea anterior surface, cornea posterior surface, thickness profile of cornea, vertex of cornea, lens, lens anterior surface, astigmatic axes of lens anterior surface, lens posterior surface, astigmatic axis of lens posterior surface, retina, anterior optical node of eye, posterior optical node of eye, optical axis of eye, line of sight of eye, pupillary axis of eye, visual axis of eye, nodal axis of eye, center of curvature of anterior corneal surface, center of curvature of posterior corneal surface, center of curvature of lens anterior surface, or lens posterior surface. At a step 860, determine alignment of non-contact eye measurement reference axes in relation to contact eye measurement reference axes in response to locations of the one or more tissue structures. At a step 865, determine one or more of an orientation or a translation of the contact measurement axes of the eye in relation to non-contact measurement axes of the eye. At a step 870, determine contact eye coordinate references of the one or more tissue structures of eye without patient interface contacting eye in response to the one or more of rotation, translation, or cyclotorsion when the patient interface contacts the eye. At a step 875, determine one or more non-contact treatment axes in response one or more of an orientation of a translation of the contact measurement axes in relation to the non-contact measurement axes. At a step 880, display the one or more non-contact treatment axes to the user. At a step 885, display locations of the one or more tissue structures of the eye measured without contact to the user, with the locations rotated and translated in response to the rotation and translation of the eye between the non-contact measurement and the contact measurement. At a step 890, determine incision profiles in response to locations of tissue structures measured without eye contact when the patient interface contacts the eye. At a step 895, determine incision profiles of capsulotomy in response to locations of tissue structures measured without eye contact when the patient interface contacts the eye.

At a step 900, align capsulotomy with visual axis of the eye shown on display. At a step 905, determine incision profiles of limbal relaxing incisions in response to locations of tissue structures without eye contact when the patient interface contacts the eye. At a step 910, align limbal relaxing incisions on the visual axis of the eye shown on display. At a step 915, incise tissue with laser beam. At a step 920, remove lens of the eye. At a step 925, display reference treatment axes. At a step 930, place intraocular lens in eye. At a step 935, align astigmatic axes of IOL with astigmatic reference treatment axes of eye on display with rotation of the IOL around the visual axis. At a step 940, align optical node of IOL with anterior optical node of eye shown on display. At a step 945, remove patient interface. At a step 950, follow up visit with patient.

FIG. 7 shows a method 700 in accordance with embodiments. Several modifications and variations can be provided, such as the steps can be performed in any order, one or more of the steps may comprise substeps, one or more steps can be removed, one or more steps can be repeated, and a person of ordinary skill in the will recognize many variations in accordance with method disclosed herein. Further, the circuitry of system 2 as described herein, for example the processor of system 2, can be configured with instructions to perform one or more of the steps of method 700, and the tangible medium of the processor may embody instructions to perform one or more of the steps of method 700. In many embodiments, the tangible medium comprises instructions of a computer readable memory having instructions of a computer program to perform one or more of the steps of method 700. Alternatively or in combination, the logic array, such as the field programmable gate array as described herein can be programmed to perform one or more of the steps of method 700. In many embodiments, the processor comprises a plurality of processors and may comprise a plurality of distributed processors.

Figure 8:
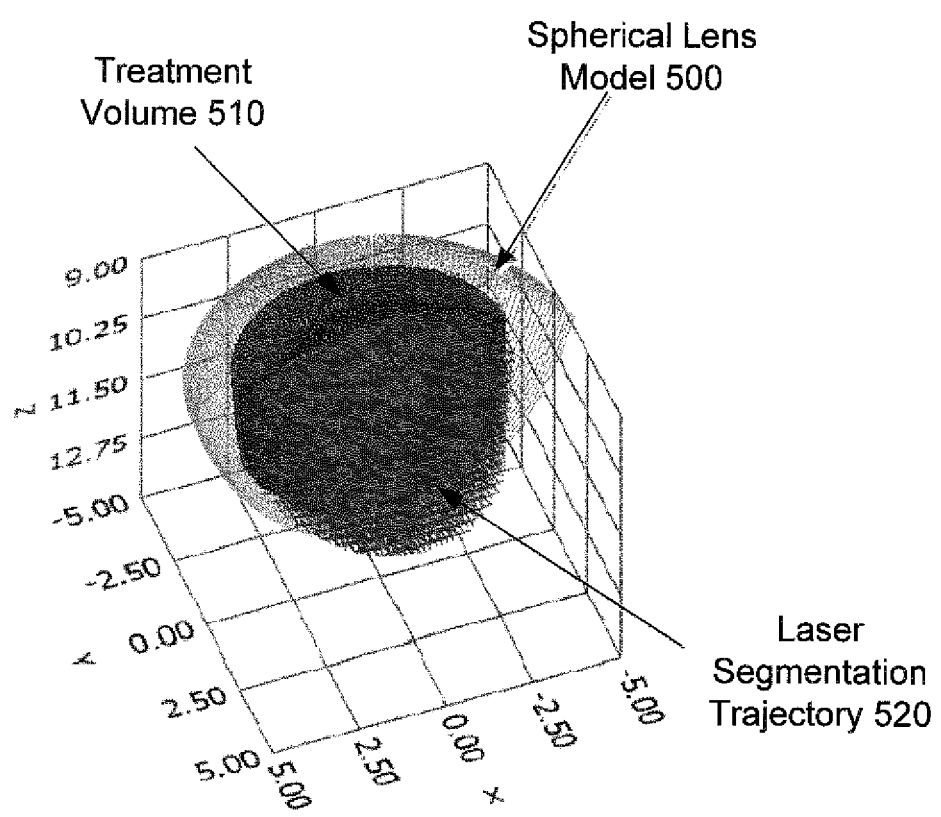
FIG. 8 is a diagram of a three dimensional spherical lens model, treatment volume and laser trajectory, in accordance with many embodiments.

FIG. 8 is a diagram of a three dimensional spherical lens model, treatment volume and laser trajectory, in accordance with many embodiments. The spherical lens model 500 includes models of the lens anterior and posterior surfaces and the elliptical model for the pupil. Spherical lens model 500 is generated based on the measured eye characteristics as described herein above, for example. Predetermined safety distances and thresholds are used to generate the treatment volume 510 inside the lens model 500. The laser segmentation (LS) trajectory 520, or fragmentation pattern, represents the laser fragmentation pattern and includes a set of position and energy settings that define the laser trajectory of the lens segmentation treatment. Typical trajectories 520 are of the order of a minute long and contain of the order of millions of points. The LS trajectory 520 is used for lens extraction in cataract surgery.

The LS trajectory 520 is determined based on a plurality of parameters. The system 2 may compute the entire LS trajectory before treatment is performed or compute and fire the laser trajectory concurrently. The LS trajectory 520 may be computed based on LS parameters including grid shape, depth, diameter, limited diameter (mm), segmentation/soft grid spacing (µm), diagnostic lens thickness (mm), spot spacing (µm), depth spacing (µm), number of cross replicates, lens anterior safe distance (µm), iris safe distance (µm), iris angle NA (deg), lens posterior safe distance (µm), anterior pulse energy (µJ), posterior pulse energy (µJ), average power (mW), and rotation angle. The rotation angle may correspond to a user custom angle or a primary incision rotation angle with respect to a machine coordinate reference system.

The depth parameter defines the treatment area and the selectable depths include OCT, diagnostic thickness or a predetermined thickness (e.g., 2.5 mm). The OCT setting uses the sphere models computed for both surfaces of the lens. Selection of diagnostic thickness allows the user to input a previously measured lens thickness. The lens posterior radius of curvature may be set to 4.5 mm when either the diagnostic thickness or predetermined thickness is selected as the depth.

The diameter parameter may be maximized without constraint to the diameter of the lens segmentation or limited so as to constrain the diameter of the lens segmentation. For the maximized diameter, the mirror diameter of the elliptical model of the iris and the sphere model of the lens is used as the lateral boundaries. The pulse energy varies linearly from posterior to anterior, as defined by the anterior and posterior pulse energy parameters.

Figure 9:
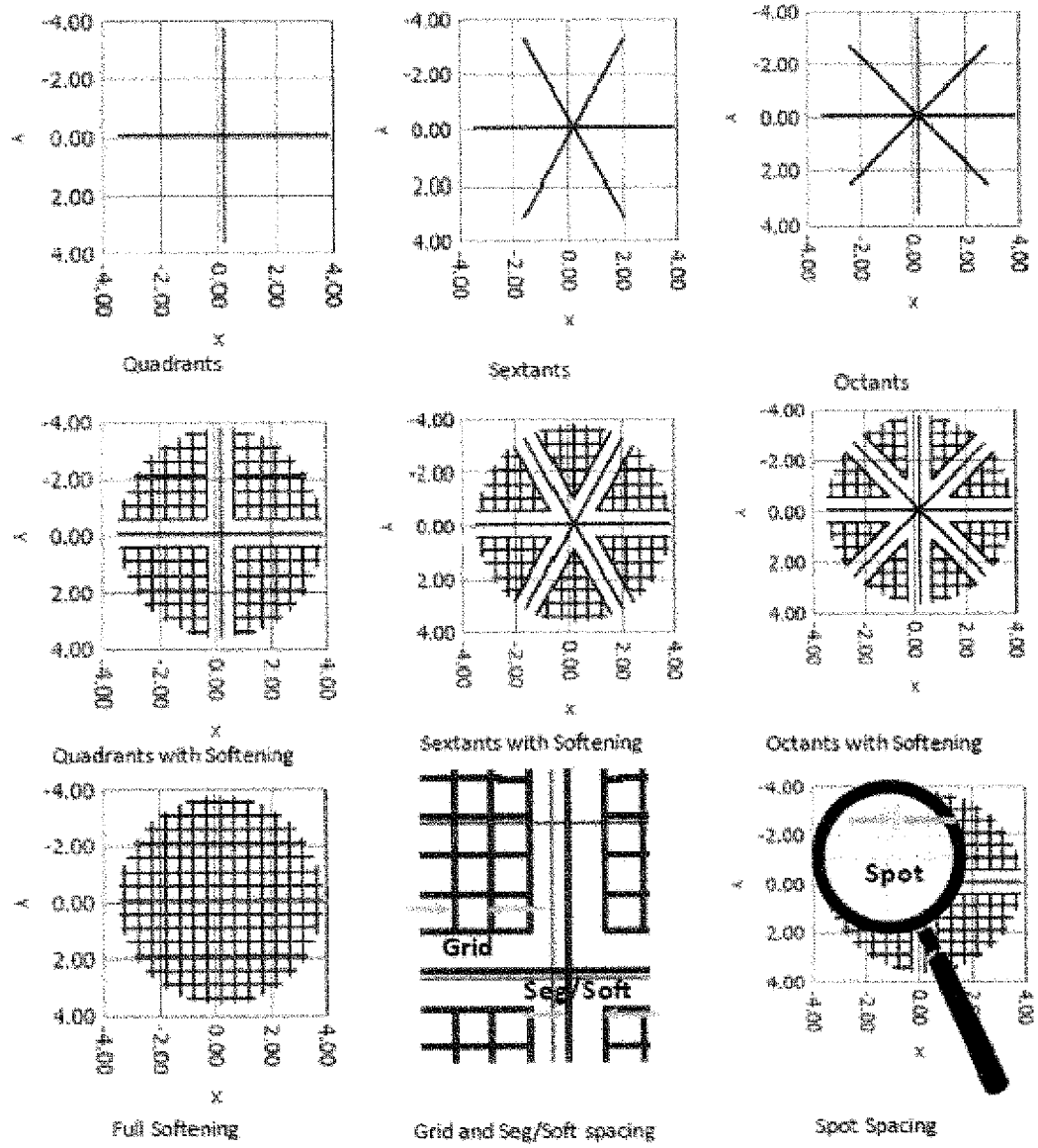
FIG. 9 is a diagram of various lens segmentation patterns, in accordance with many embodiments.

FIG. 9 is a diagram of various lens segmentation patterns, in accordance with many embodiments. The grid shape parameter allows selection of quadrant, sextant, octant, full softening, quadrant with softening, sextant with softening and octant with softening. These grid shapes are illustrated in FIG. 9. The grid spacing parameter defines the density of the grid. The segmentation/soft grid spacing parameter defines the separation of the grid from the center of the fragmentation pattern (e.g., the middle cross). The spot spacing parameter defines the distance between laser burn spots.

In some embodiments, the grid shapes and softening is asymmetrical. In other words, different portions of the pattern may have a different shape and softening than other portions of the pattern.

Figure 10:
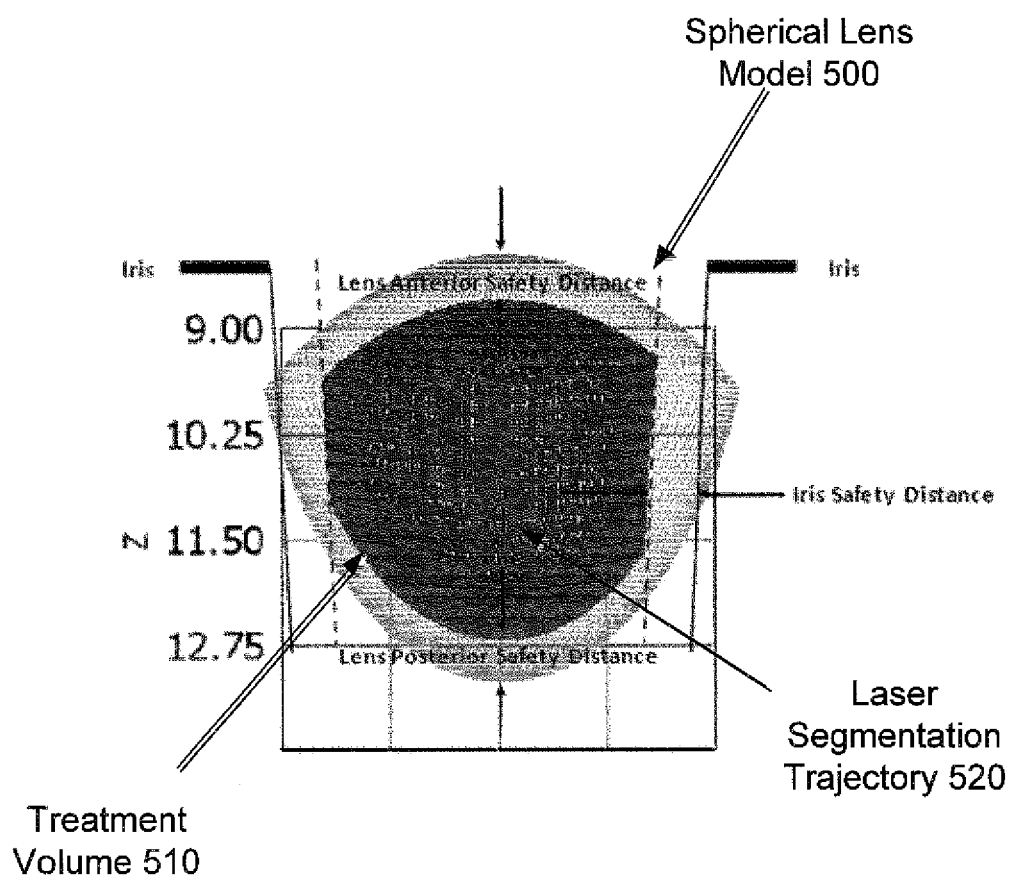
FIG. 10 is a diagram illustrating lens segmentation safety distances, in accordance with many embodiments.

FIG. 10 is a diagram illustrating lens segmentation safety distances, in accordance with many embodiments including the lens segmentation trajectory 520 (red), treatment volume 510 (blue), and spherical lens model 500 (green). The numerical aperture of the system 2 creates a tilted safety zone under the iris, which angles from the vertical by the iris angle parameter.

Figure 11A:
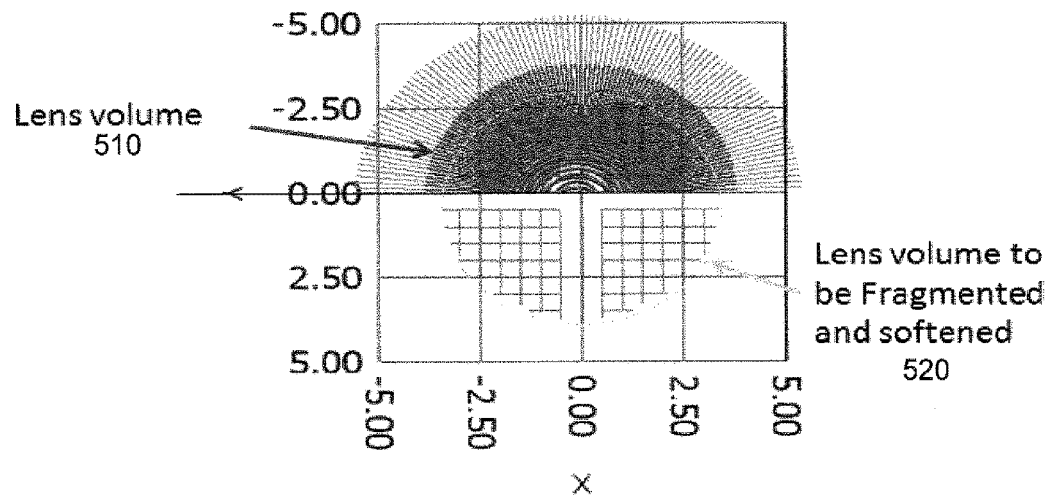
FIGS. 11A-11B are diagrams illustrating lens fragmentation pattern rotation, in accordance with many embodiments.
Figure 11B:
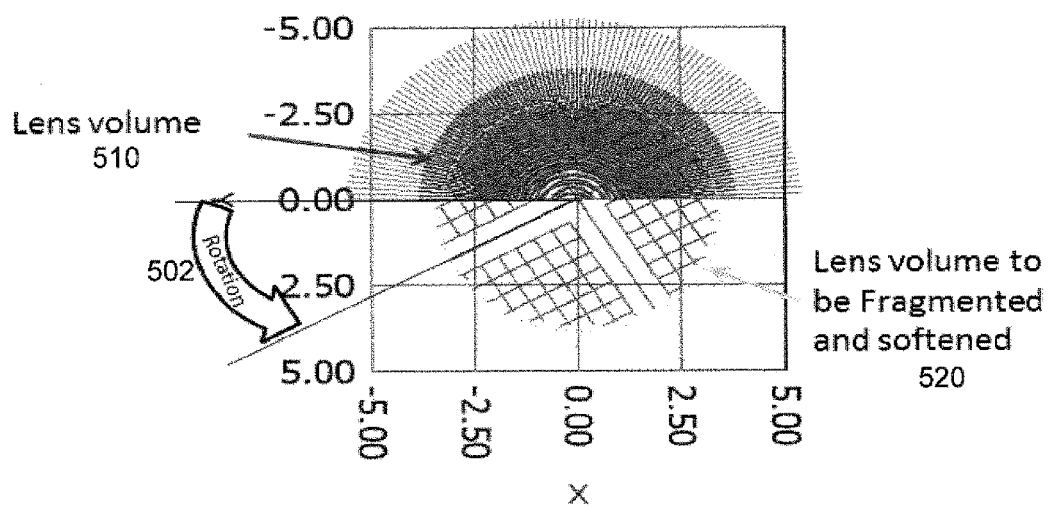

FIGS. 11A-11B are diagrams illustrating lens fragmentation pattern rotation, in accordance with many embodiments. FIG. 11A illustrates a lens fragmentation pattern that may be computed when the rotation angle parameter is set to a default value, such as zero degrees. This corresponds to no rotation of the laser segmentation trajectory 520 with respect to the machine coordinate reference system. In this case, the LS trajectory 520 is aligned along the Y-axis of the machine coordinate reference system. Alternatively, the fragmentation pattern may be aligned along the X-axis or any other predetermined reference axis.

Figure 17:
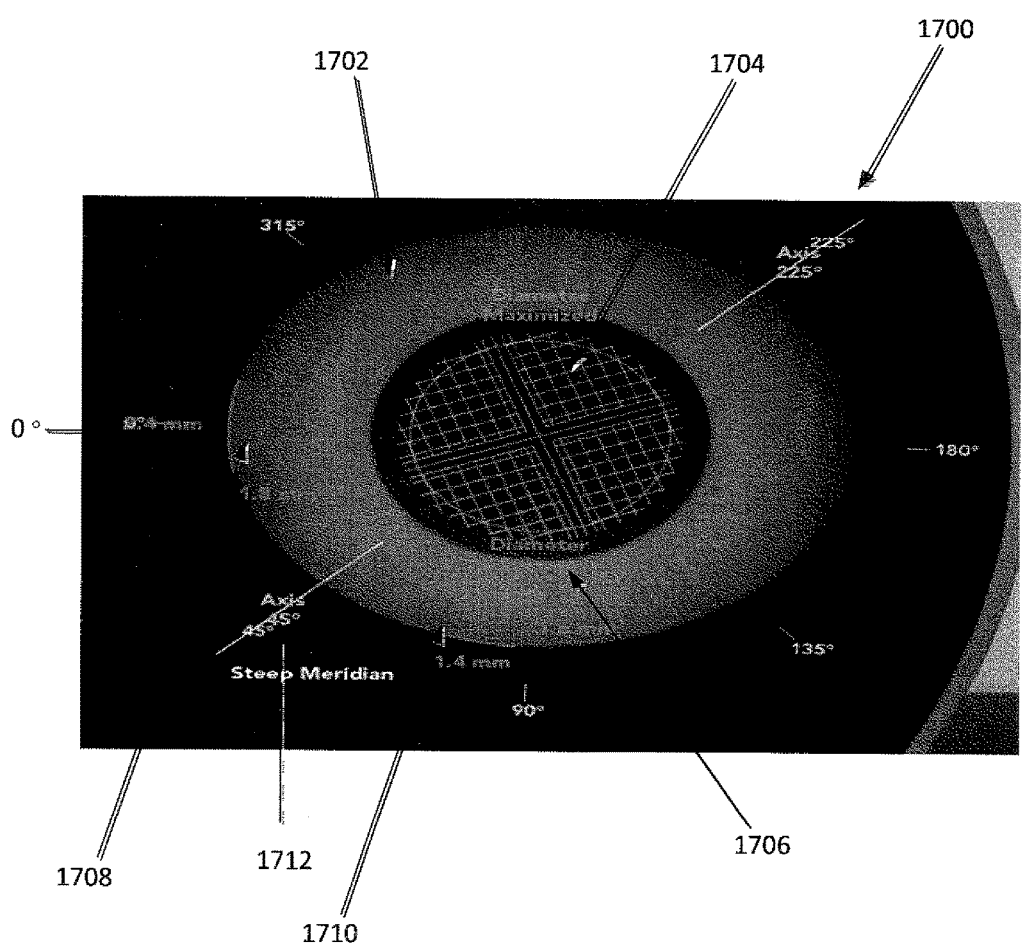
FIG. 17 is a GUI display illustrating lens fragmentation rotation, in accordance with many embodiments.

In FIG. 11B, a user may input a custom value (e.g., 30 degrees) for the rotation angle 502 of the fragmentation pattern with respect to the machine coordinate reference system. FIG. 17 is a diagram illustrating a rotated lens fragmentation pattern, in accordance with many embodiments. The user selects the rotation angle to align with the rotation angle of the primary incision. In other words, the rotation angle is selected so that the lens fragmentation axis is aligned with the primary corneal incision. In doing so, the lens fragmentation pattern is preferably aligned with the phaco tip and incision so as to reduce or eliminate the need for the surgeon to perform manual rotation of the lens during cataract surgery.

The process for generating a rotated lens fragmentation pattern may be briefly summarized as follows. First, the geometrical boundaries of the spherical model 500, including the lens anterior surface fit, lens posterior surface fit, iris, LS center, are rotated about the LS center by the negative of the primary incision rotation angle. For example, if the primary incision is at a 30 degree angle relative to the machine coordinate reference system, then the spherical model 500 is rotated by −30 degree angle. The LS trajectory 520 is generated based on inputted segmentation parameters and then aligned with the machine coordinate reference system (0 degree) such that the rotated spherical lens model 500 is overlaid by the unrotated LS trajectory 520. Then, both the spherical lens model 500 and the LS trajectory 520 are rotated forward by the rotation angle (30 degrees). The resultant LS trajectory 520 is now rotated so as to be aligned with the primary incision rotation angle. The spherical lens model 500 returns to its original position while the LS trajectory 520 is rotated by the desired amount. Rotation is discussed in further detail in FIGS. 12-14.

Figure 12:
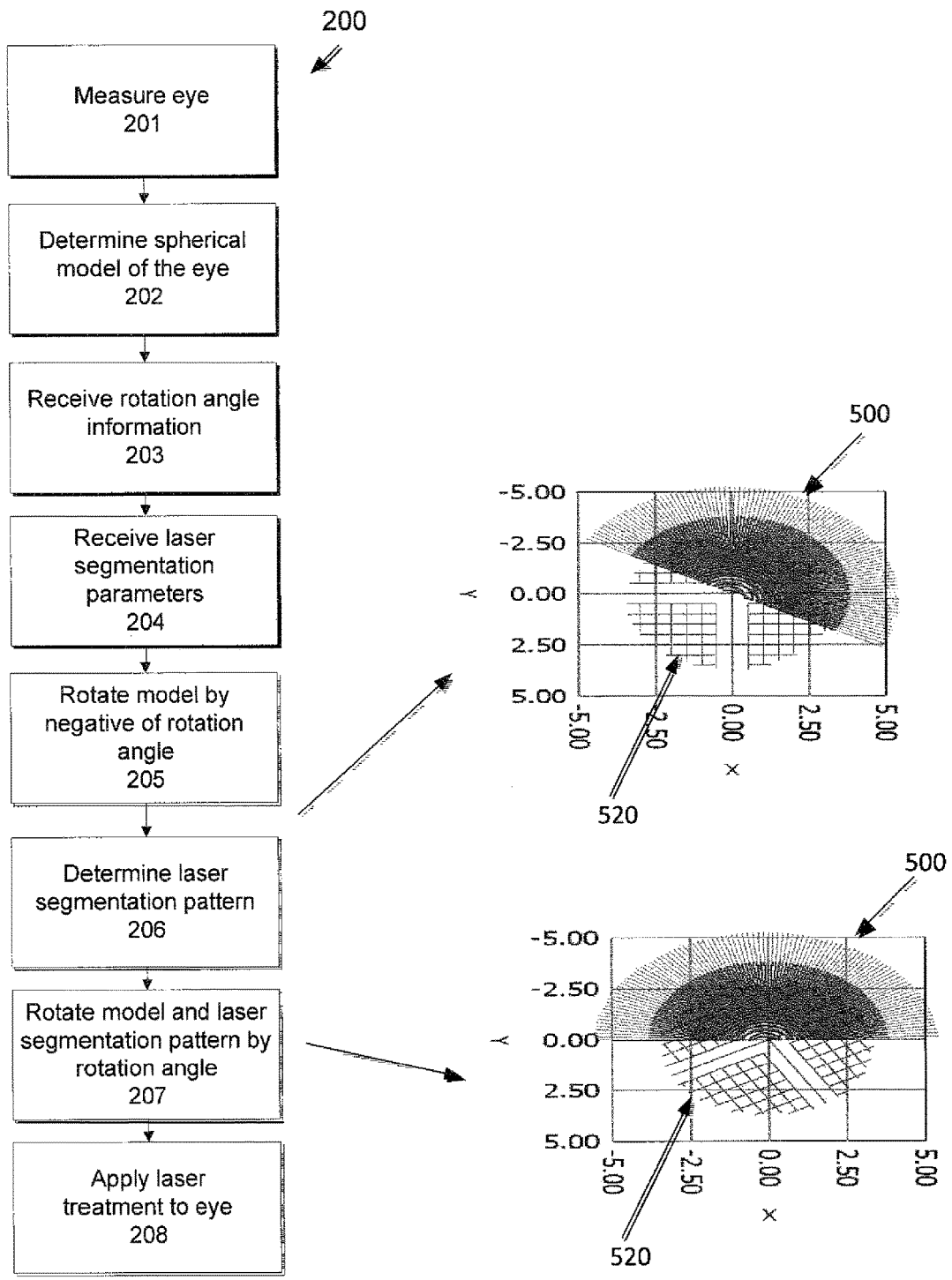
FIG. 12 is a flowchart illustrating a method of rotating a lens fragmentation pattern, in accordance with many embodiments.

FIG. 12 is a flowchart illustrating a method of rotating a lens fragmentation pattern, in accordance with many embodiments. Several modifications and variations can be provided, such as the steps can be performed in any order, one or more of the steps may comprise substeps, one or more steps can be removed, one or more steps can be repeated, and a person of ordinary skill in the will recognize many variations in accordance with method disclosed herein. Further, the circuitry of system 2 as described herein, for example the processor of system 2, can be configured with instructions to perform one or more of the steps of method 200, and the tangible medium of the processor may embody instructions to perform one or more of the steps of method 200. In many embodiments, the tangible medium comprises instructions of a computer readable memory having instructions of a computer program to perform one or more of the steps of method 200. Alternatively or in combination, the logic array, such as the field programmable gate array as described herein can be programmed to perform one or more of the steps of method 200. In many embodiments, the processor comprises a plurality of processors and may comprise a plurality of distributed processors.

At step 201, the patient is docked and the eye is measured by the system 2, such as by the OCT ranging subsystem 46. Features such as the surfaces of the cornea, the anterior and posterior lens and the iris are measured. The measured physical dimensions of the eye are mapped onto an eye coordinate reference system. Eye measurements may be performed as described above in the method of FIG. 7. The laser system 2 then maps physical coordinates of the eye 43 in the eye coordinate reference system to a machine coordinate reference system. At step 202, the system 2 determines a spherical model of the eye in the machine coordinate reference system by fitting a set of geometric surfaces such as ellipsoids, spheres and toroids, to the measured eye data. The eye model includes the spherical lens model 500 and treatment volume 510.

At step 203, the user inputs a primary corneal incision angle relative to the machine coordinate reference system. For example, the inputted rotation angle is relative to the 0° reference axis of the machine coordinate reference system illustrated in FIG. 17. For ease of explanation, this 0° axis is the reference axis of the machine coordinate reference system, although any reference axis may be chosen. In some embodiments, the reference axis is aligned with a fiducial of the laser system 2. The user may input, for instance, that the primary corneal incision is 30 degrees relative to the reference axis of the machine coordinate system. The system 2 will use this primary corneal incision angle to automatically determine the rotation of the lens fragmentation pattern so as to align the primary incision with the lens fragmentation. Alternatively, the user inputs that the rotation angle of the lens fragmentation is a predetermined rotation value, such as 0° (no rotation), or a custom angle different from the incision angle. In this case, the predetermined rotation value or custom angle may or may not align with the rotation angle of the primary corneal incision.

At step 204, the system 2 receives the laser segmentation trajectory parameters such as those inputted by a user and illustrated in FIG. 9. At step 205, the eye model is rotated by the negative of the rotation angle relative to the machine coordinate reference system. At step 206, the laser segmentation trajectory 520 is determined and aligned with the reference axis of the machine coordinate reference system. A skeleton map of the segmentation trajectory may be constructed in step 206. The skeleton map includes a set of initial and end points that are used to generate the line segments, but does not include the line segments themselves. The laser segmentation trajectory 520 at this step is not rotated by the rotation angle. If a quadrant segmentation pattern is selected, such as shown in FIG. 9, then the quadrant axes are aligned to the horizontal and vertical axes of the machine coordinate reference system. As shown in FIG. 12, the model 500 is rotated while the laser segmentation trajectory 520 is aligned with the machine coordinate reference system. The laser segmentation trajectory may be determined under the frame architecture as described in detail in FIG. 19.

At step 207, the laser segmentation trajectory 520 and the eye model are both rotated forward by the inputted rotation angle. After the rotation, the eye model is re-aligned with the reference axis of the machine coordinate reference system. Thus, the laser segmentation trajectory 520 is rotated by the desired rotation angle. In the frame architecture, every line in the segmentation trajectory 520 is defined by an initial and final point. Accordingly, the rotation of the trajectory 520 in step 207 rotates the set of initial and final points, and not the lines themselves, thereby saving computation cycles. Once the final rotated laser segmentation trajectory 520 is determined at step 207, the lines between the set of initial and final points may be filled.

Alternatively, the machine coordinate reference system may be rotated by the negative of the rotation angle at step 205 instead of rotating the eye model. The laser segmentation trajectory 520 at step 206 is determined based on the unrotated machine coordinate reference system. Then, at step 207, the rotated machine coordinate reference system and the laser segmentation trajectory 520 are rotated forward by the rotation angle. In either case, the laser segmentation trajectory 520 is rotated to align with the primary incision rotation angle. Preferably, the laser segmentation trajectory 520 is rotated to align with the angle of the primary corneal incision. At step 208, the rotated laser fragmentation pattern is applied in a laser beam to fragment the lens during cataract surgery.

The rotation and alignment of the lens fragmentation pattern as described above facilitates lens removal due to the angle of occlusion and other fluidic properties. A fragmentation that is aligned with the primary corneal incision also reduces the rotation of the nucleus performed by the surgeon by reducing the manipulation of the phaco tip and sleeve in the incision. Accordingly, this method may reduce incision stretch and improve would sealing, resulting in easier and safer cataract surgery.

The rotation of the lens fragmentation pattern as described above also provides faster computation and requires less memory and buffering since the skeleton map of initial and end points is rotated by the rotation angle rather than rotation of each of the line segments themselves. After the rotation of the LS trajectory is completed, the turnarounds and line segments are computed.

Figure 13A:
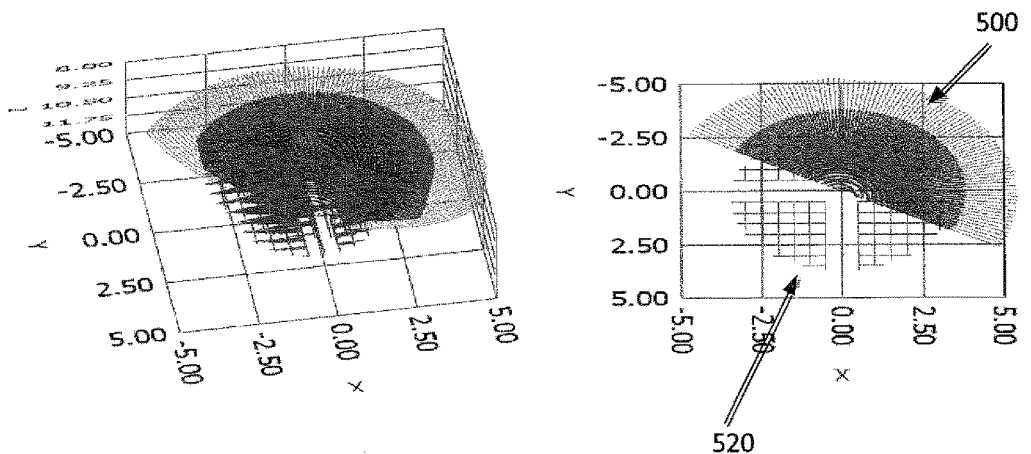
FIGS. 13A-13B are diagrams illustrating rotation of lens fragmentation patterns, in accordance with many embodiments.
Figure 13B:
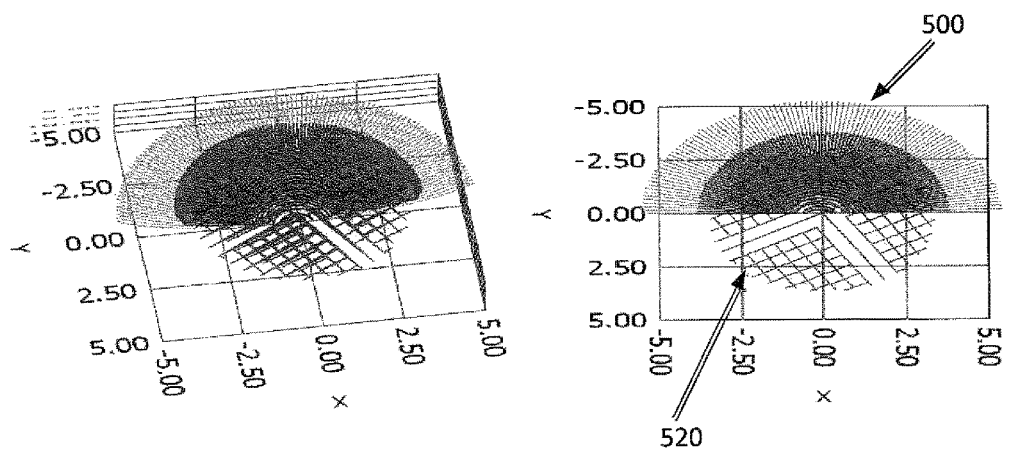

FIGS. 13A-13B are diagrams illustrating rotation of lens fragmentation patterns, in accordance with many embodiments. FIG. 13A illustrates the results of intermediary steps 205 and 206 in a two-dimension plane and three-dimensional space where the eye model is rotated by the incision rotation angle relative to the machine coordinate reference system while the laser segmentation trajectory is aligned with the machine coordinate reference system. FIG. 13B illustrates the laser segmentation trajectory 520 to be applied as treatment where the eye model is aligned with the machine coordinate reference system and the laser segmentation trajectory 520 is rotated by the inputted rotation angle relative to the machine coordinate reference system.

Figure 14:
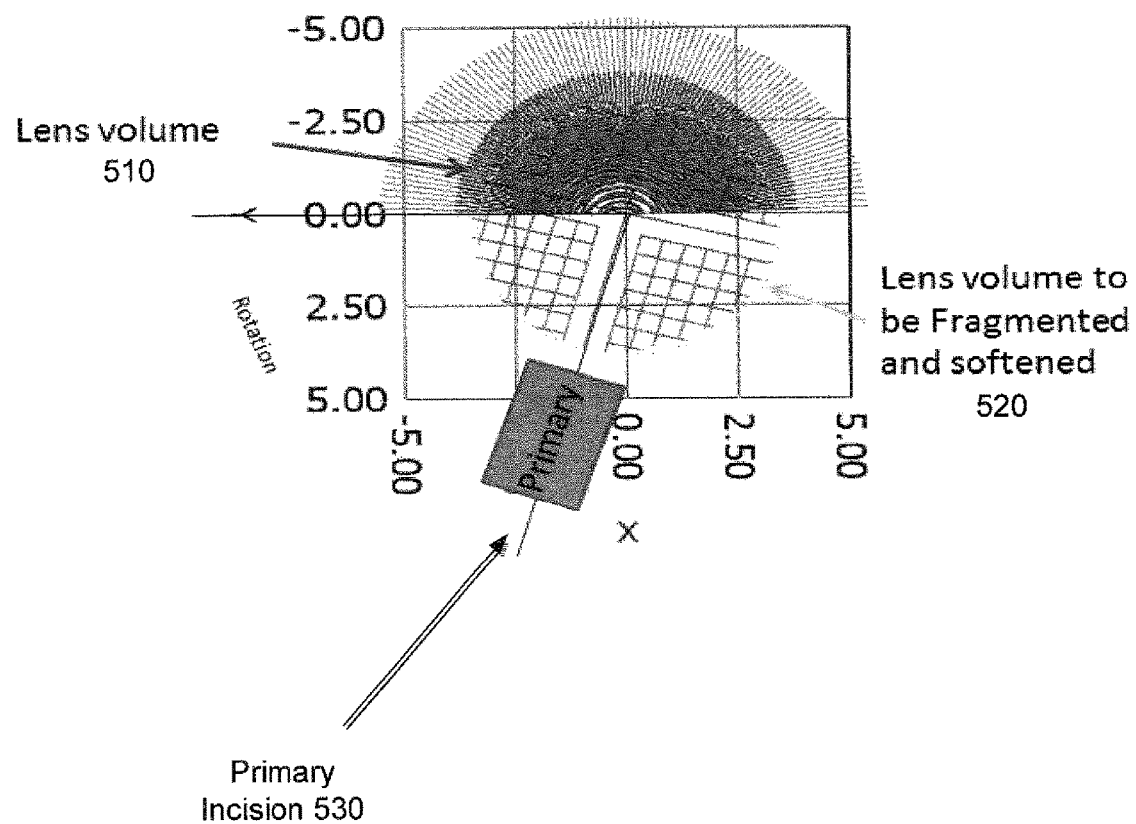
FIG. 14 is a diagram illustrating a rotated lens fragmentation pattern, in accordance with many embodiments.

FIG. 14 is a diagram illustrating a rotated lens fragmentation pattern, in accordance with many embodiments. In FIG. 14, the rotated laser segmentation trajectory 520 is aligned with the rotation angle of the primary corneal incision 530. In this manner, the phaco tip inserted into the primary corneal incision is aligned with the lens fragmentation pattern to eliminate unnecessary rotation of the lens. The first segmentation piece of the lens to be removed is preferably aligned opposite the phaco incision, although the user may select a custom angle as well.

Figure 15A:
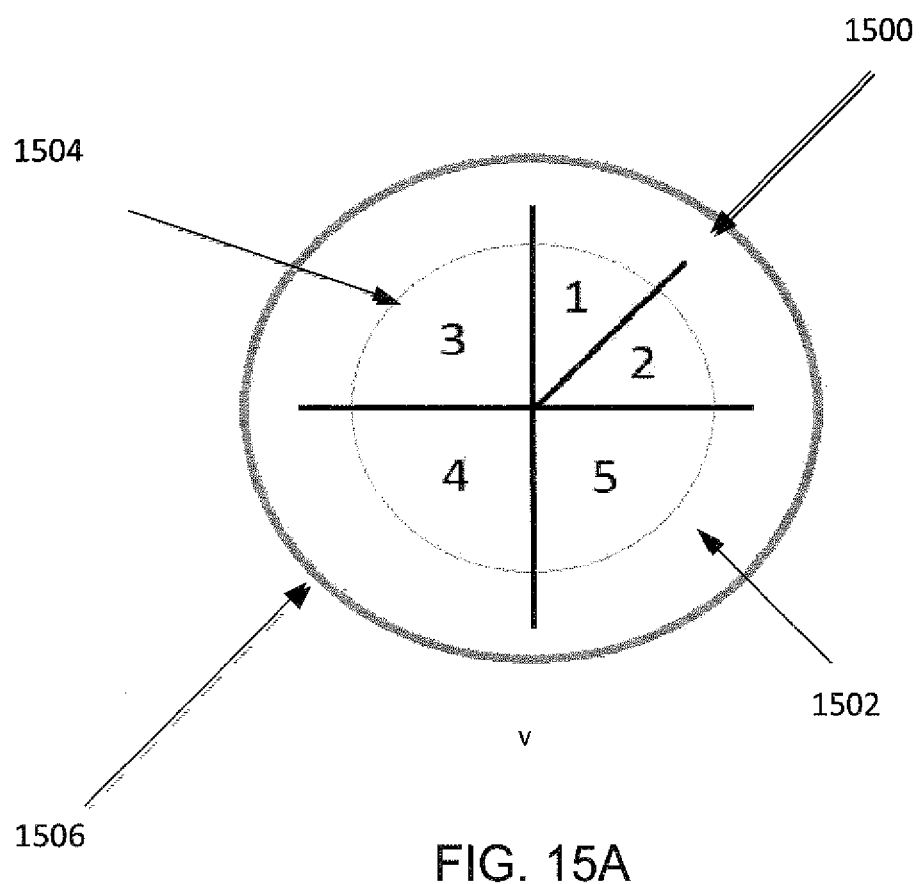
FIGS. 15A-15B are diagrams illustrating segmentation and softening, in accordance with many embodiments.
Figure 15B:
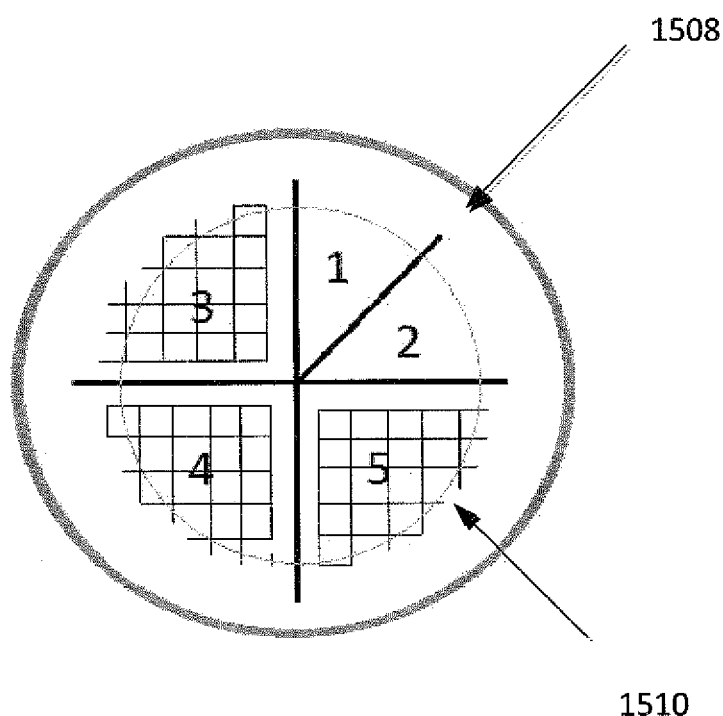

FIGS. 15A-15B are diagrams illustrating segmentation and softening, in accordance with many embodiments. In FIG. 15A, a model of the eye and lens fragmentation pattern is provided. In some embodiments, the fragmentation and softening of the laser trajectory is asymmetrical in that different portions of the fragmentation pattern have different sized segments and softening. In FIG. 15A, the laser segmentation pattern is first divided into quadrants. Three out of the four quadrants in a second portion 1502 (3, 4, 5) are identical. However, one of the four quadrants in a first portion 1500 is bisected so as to provide two octants (1, 2). The diameters of the capsulotomy 1504 and eye 1506 are outlined.

As such, FIG. 15A illustrates a laser fragmentation pattern including a first portion including two octants and a second portion including three quadrants. By providing a first portion with two smaller octant pieces, the first portion may be removed first during the lens extraction of a cataract surgery. The smaller size of the octants facilitates removal by the surgeon through the small capsulotomy 1504. After removing the first portion, the difficulty in removal of the remaining pieces is reduced since there is more room in the capsular bag for the surgeon to maneuver and manipulate the remaining second portion pieces (3, 4, 5). As a result of the asymmetrical fragmentation pattern, removal of the initial lens piece (1, 2) is eased without affecting removal of the remaining lens pieces.

FIG. 15B illustrates a similar fragmentation pattern as FIG. 15A but with different softening patterns. In particular, first portion 1508 is divided into octant pieces (1, 2) with no softening provided. The second portion 1510 includes the remaining three quadrants (3, 4, 5) with softening. As opposed to a lens fragmentation that is entirely softened, the phaco tip can easily purchase the smaller, unsoftened pieces in the first portion 1508. The unsoftened first portion 1508 provides uninterrupted tissue with better occlusion properties for the phaco tip to pull out of the phaco incision. As the initial portion of lens to be removed is often the most difficult, it is advantageous to reduce the size and maintain the hardness of the first piece of lens to be extracted by the phaco tip. A smaller, unsoftened lens portion is easiest to extract as the initial piece of the extracted lens, while the remaining portions of the lens may possess a different fragmentation and softening pattern. However, any combination of asymmetrical fragmentation patterns are contemplated where at least two portions of a lens fragmentation pattern differ in fragmentation and/or softening from each other.

Figure 16:
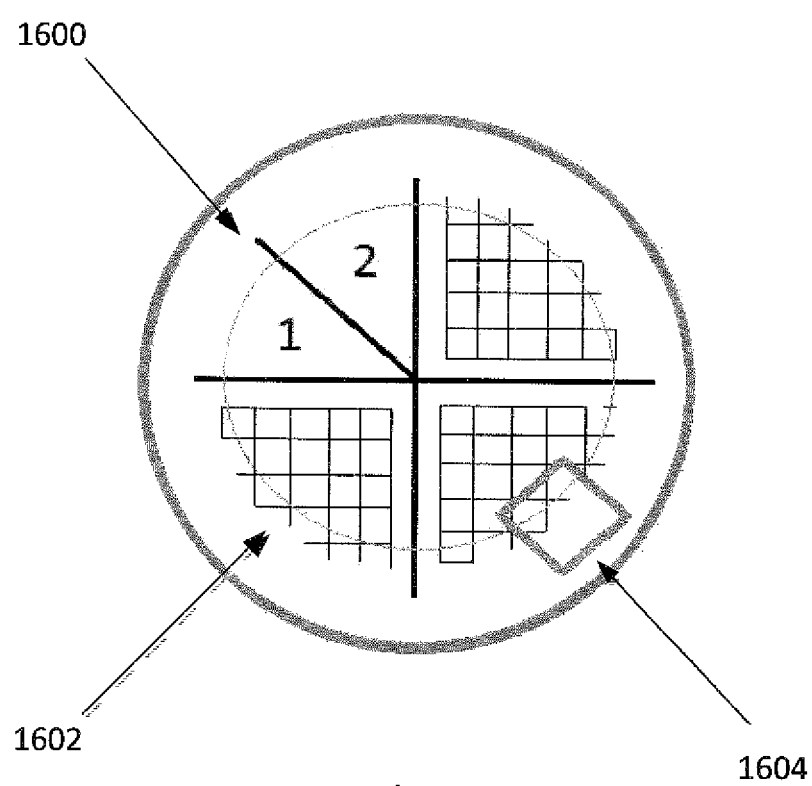
FIG. 16 is a diagram illustrating lens rotation, segmentation and softening, in accordance with many embodiments.

FIG. 16 is a diagram illustrating lens rotation, segmentation and softening, in accordance with many embodiments. FIG. 16 illustrates the same fragmentation and softening as in FIG. 15, and further includes rotation of the laser segmentation trajectory for alignment with the primary phaco incision 1604. In particular, the first portion 1600 that is to be removed first is rotated to be opposite the incision 1604. In FIG. 16, after removal of the first portion 1600, the surgeon may physically move one of the quadrants of the second portion 1602 over to the initial position of the first portion 1600 for subsequent removal by the phaco tip. The final two quadrants may then be repositioned and removed with relative ease. In this manner, the lens may be extracted without rotation whatsoever. Lens extraction in cataract surgery is optimized by reducing the size of the initial portion of lens removed, ensuring that the initial portion is unsoftened to promote the whole extraction of the initial portion, and rotating the lens fragmentation pattern such that the initial portion is aligned opposite the phaco incision thereby reducing lens rotation.

FIG. 17 is a GUI display illustrating lens fragmentation rotation, in accordance with many embodiments. The GUI display 1700 allows a user to visualize the primary incision, steep meridian, capsulotomy and lens fragmentation pattern. The horizontal axis corresponds to 0° and 180°. An image of the eye 1702 is overlaid with the rotated lens fragmentation pattern 1704, capsulotomy 1706, primary corneal incision 1708, secondary (sideport) corneal incision 1710, and steep meridian 1712. As shown in FIG. 17, the lens fragmentation 1704 is rotated so as to be aligned with the primary corneal incision 1708.

Figure 18:
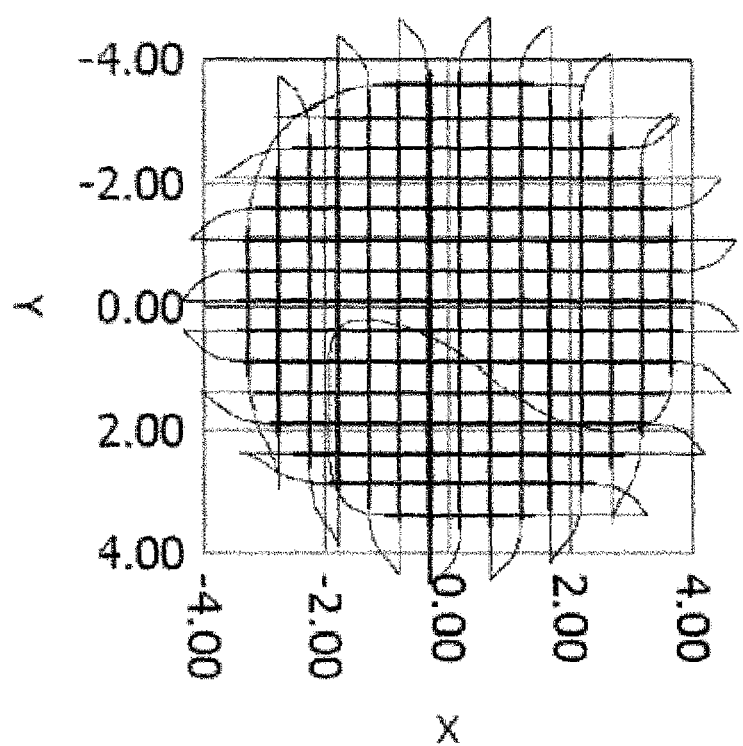
FIG. 18 is a diagram illustrating turn-arounds of a lens fragmentation pattern, in accordance with many embodiments.

FIG. 18 is a diagram illustrating turn-arounds of a lens fragmentation pattern, in accordance with many embodiments. The patterns presented in FIG. 18 are constructed with a single trace of the laser through use of a pulse picker off in a manner similar to drawing on a paper without lifting the pen. In between grid lines and layers, the laser is commanded with the pulse picker off. Laser spots are represented as thicker lines while the turn-arounds are represented by the thinner lines. Turn-arounds are constructed by a 3D bang-bang algorithm that given the initial and final velocities and positions. The bang-bang algorithm defines a trajectory between an initial point and velocity to a final point and velocity that have either constant velocity (system maximum) or constant acceleration (system maximum).

Figure 19:
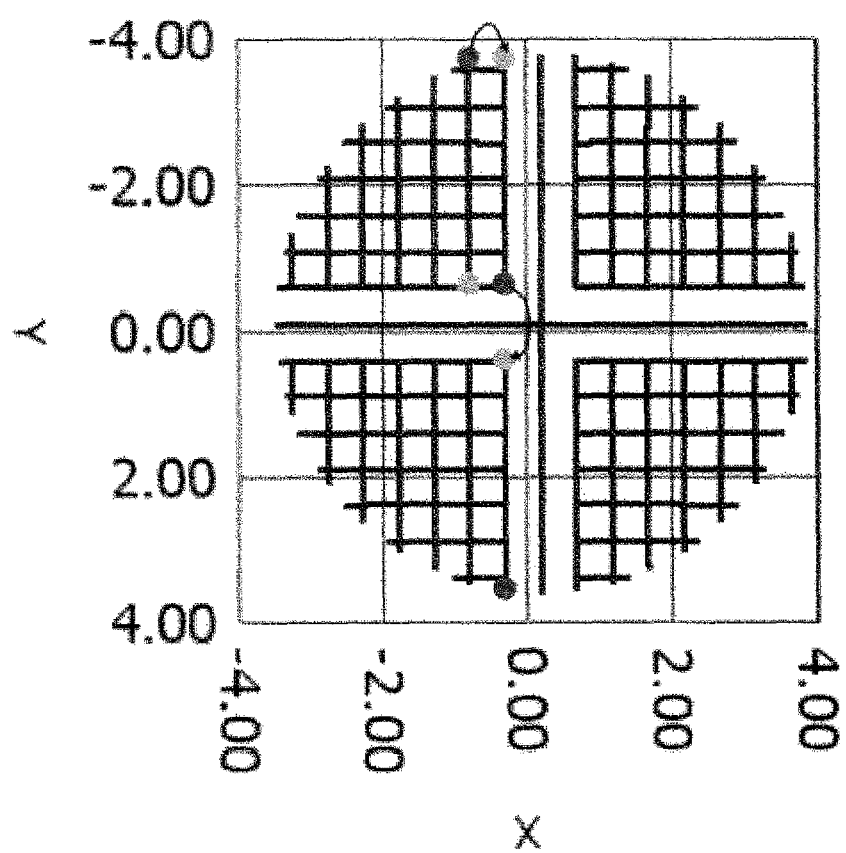
FIG. 19 is a diagram illustrating a frame architecture of a lens fragmentation pattern, in accordance with many embodiments.

FIG. 19 is a diagram illustrating a frame architecture of a lens fragmentation pattern, in accordance with many embodiments. Under the frame architecture, the lens segmentation trajectory is computed in two steps. On the first step, a road map of the trajectory is computed (the frame). The trajectory is divided into lines and the initial and final points of every line is computed. This is enough information to compute the output power levels analytically and define the turn-arounds between lines. It also contains information to determine if the trajectory is possible or if error conditions are generated. On a second step, (the detail) at the firing time, the trajectory is divided into sets and while one set is fired, the next set is computed. Adequate buffering ensures continuity of the cut.

Figure 20:
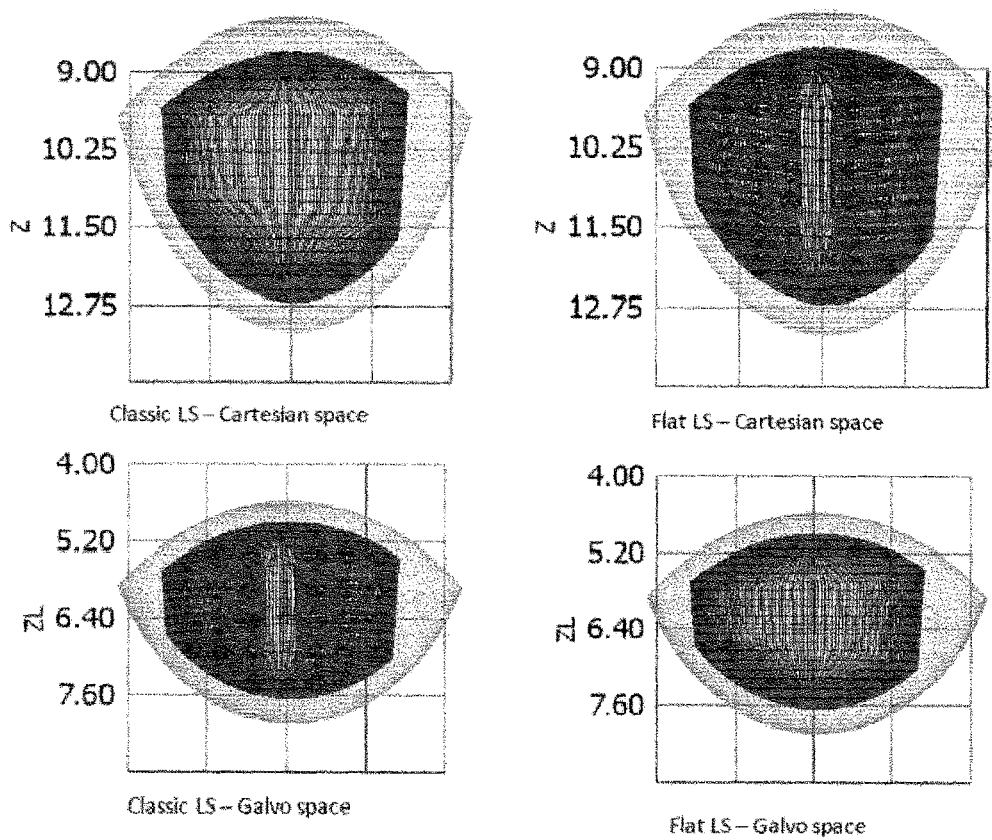
FIG. 20 is a diagram illustrating operation modes of a lens fragmentation pattern, in accordance with many embodiments.

FIG. 20 is a diagram illustrating operation modes of a lens fragmentation pattern, in accordance with many embodiments. FIG. 20 illustrates the differences between the Classic and the Flat LS operation modes. The Classic LS has to move the Z1 motor very aggressively in order to maintain horizontal layers in the patients lens. The Flat LS leaves the Z1 motor stationary on every layer to provide parabolic lens segmentation layers on the patient's lens. The Flat LS delivers a more precise cut since the Z1 is static on every layer. In the Classic LS, the pattern is defined as flat Cartesian layers that correspond to flat layers in the lens. For the Flat LS segmentation, layers correspond to flat layers in galvo space that correspond to parabolic traces in the lens.

The Flat LS is realized by transforming the anterior and posterior surfaces of the lens to a hybrid space defined in Cartesian X, Y and galvo Z1. This is accomplished by sampling points on the two Cartesian spheres that define the lens and transforming these points into galvo space. The original Cartesian X,Y are kept with insertion of the galvo Z1. A new fit is done to these points and the new spheres are constrained to be interior to these points. Horizontal parameters are kept the same, but z dependent parameters are wharped according to Look Up Tables (LUTs).

The Frames for the LS is computed, that is, initial and final points for every line are defined in Cartesian X,Y and galvo Z1. Then these set of points are wharped to galvo Xm, Ym, and ZL. The system 2 accepts points in galvo coordinates, completes lines in galvo coordinates and produces turn-arounds in galvo coordinates.

The Classic LS produces the initial and final points of the lines in the Frames in Cartesian space. The system 2 joins these points in Cartesian space but produces turn-arounds in galvo space. Then every point is transformed, point by point, from Cartesian to galvo coordinates. Turn-arounds are left in galvo space.

Although the above steps show a system and method of rotating a lens fragmentation pattern in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the treatment.

One or more of the steps of the method of rotating a lens fragmentation pattern may be performed with the circuitry as described herein, for example one or more of the processor or logic circuitry such as the programmable array logic for field programmable gate array. The circuitry may be programmed to provide one or more of the steps of method of rotating a lens fragmentation pattern, and the program may comprise program instructions stored on a computer readable memory or programmed steps of the logic circuitry such as the programmable array logic or the field programmable gate array, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of generating a rotated lens fragmentation pattern for a lens of an eye, comprising:
   determining a spatial model of the eye in an eye coordinate reference system based on a measurement beam;

mapping the spatial model from the eye coordinate reference system to a machine coordinate reference system;

receiving a rotation angle of a corneal incision relative to a reference axis of the machine coordinate reference system;

determining a pre-rotated lens fragmentation pattern for the lens of the eye based on a plurality of laser fragmentation parameters;

determining a first rotation angle based on the rotation angle of the corneal incision and a rotation angle of the pre-rotated lens fragmentation pattern relative to the reference axis of the machine coordinate reference system;

rotating the spatial model by a negative of the first rotation angle;

rotating the pre-rotated lens fragmentation pattern and the spatial model by the first rotation angle such that the spatial model is aligned with the reference axis of the machine coordinate reference system and the rotated lens fragmentation pattern is aligned with the corneal incision; and generating a laser beam by a laser source based on the rotated lens fragmentation pattern.

2. The method of claim 1, wherein the rotated lens fragmentation pattern defines a first lens portion to be extracted first that is aligned opposite the corneal incision.

3. The method of claim 1, wherein the rotated lens fragmentation pattern is asymmetrical.

4. The method of claim 1, wherein the rotated lens fragmentation pattern includes a first portion and a second portion having at least one of a different segmentation pattern and softening pattern.

5. The method of claim 1, wherein the rotated lens fragmentation pattern includes a first unsoftened portion and a second softened portion.

6. The method of claim 1, wherein the rotated lens fragmentation pattern includes a first portion defining two octants and a second portion defining three quadrants.

7. The method of claim 1, wherein the rotated lens fragmentation pattern includes a first portion defining two unsoftened octants and a second portion defining three softened quadrants.

8. The method of claim 1, wherein the first rotation angle is based on user input.

* * * * *